(12) United States Patent
Iwatsubo et al.

(10) Patent No.: US 8,173,775 B2
(45) Date of Patent: May 8, 2012

(54) COLLAGEN-LIKE PROTEIN CLAC, A PRECURSOR THEREOF, AND GENES ENCODING THE SAME

(75) Inventors: Takeshi Iwatsubo, Tokyo (JP); Tadafumi Hashimoto, Tokyo (JP); Yasuo Nagai, Osaka (JP)

(73) Assignees: Takeshi Iwatsubo (JP); Eisai R & D Management Co., Ltd. (JP)

( * ) Notice: Subject to any disclaimer, the term of this patent is extended or adjusted under 35 U.S.C. 154(b) by 0 days.

(21) Appl. No.: 12/985,917

(22) Filed: Jan. 6, 2011

(65) Prior Publication Data

US 2011/0137013 A1 Jun. 9, 2011

Related U.S. Application Data

(60) Continuation of application No. 12/329,171, filed on Dec. 5, 2008, now Pat. No. 7,888,076, which is a division of application No. 10/203,561, filed on Aug. 12, 2002, now Pat. No. 7,514,542.

(30) Foreign Application Priority Data

Feb. 14, 2000 (WO) ......................... PCT/JP00/00788

(51) Int. Cl.
*C07K 14/435* (2006.01)
*C07K 14/705* (2006.01)
(52) U.S. Cl. ...................................................... 530/350
(58) Field of Classification Search .................. None
See application file for complete search history.

(56) References Cited

U.S. PATENT DOCUMENTS 6,639,063 B1 10/2003 Edwards et al.

OTHER PUBLICATIONS

Pihlajaniemi T et al. The alpha1 chain of type XIII collagen consists of three collagenous and four noncollagenous domains, and its primary transcript undergoes complex alternative splicing. J Biol Chem, 1990; 265(28):16922-16928.*
International Search Report; PCT/JP2001/001014; May 15, 2001.
International Preliminary Examination Report; PCT/JP2001/001014; Mar. 26, 2002.
European Examination Report dated Feb. 5, 2004.
Mann, D.M. et al., Acta Neuropathol, "Atypical amyloid (Aβ) deposition in the cerebellum in Altzheimer's disease: an immunohistochemical study using end-specific Aβ monoclonal antibodies", (Berl) vol. 91, No. 6, (1996), pp. 647-653.
El Koury, J. et al. "Scavenger Receptor-Mediated Adhesion of Microglia to β-Amyloid Fibrils", Letters to Nature, vol. 382, Aug. 22, 1996, pp. 716-719.
Neepert, M. et al. "Cloning and Expression of a Cell Surface Receptor for Advanced Glycosylation End Products of Proteins", The Journal of Biological Chemistry, vol. 267, No. 21, Jul. 25, 1882, pp. 14998-15004.
Sun, Yuling et al. "Glial Fibrillary Acid Protein-Apolipoprotein E (apoE) Transgenic Mice: Astrocyte-Specific Expression and Differing Biological Effects of Astrocyte-Secreted apoE3 and apoE4 Lipoproteins", The Journal of Neuroscience, May 1, 1998, 18(9), pp. 3261-3272.
Yan, S.D. et al., "Amyloid-β Peptide-Receptor for Advanced Glycation Endproduct Interaction Eliccits Neuronal Expression of Macrophage-Colony Stimulating Factor: a Proinflammatory Pathway in Alzheimer Disease", Proc. National Acad. Sci. USA, vol. 94, May 1997, pp. 5296-5301.
Database Embl. Online!, MRNA 1190 BP, Feb. 8, 2001 Retrieved from EBI Database Accession No. AKO12466.
Kodama, T. et al. "Type I Macrophage Scavenger Receptor Contains Alpha-Helical and Collagen-Like Coiled Coils" Nature Macmillan Journals Ltd. London GB, vol. 343, Feb. 8, 1990, pp. 531-535.
Hashimoto, T. et al. "CLAC: A Novel Alzheimer Amyloid Plaque Component Derived From a Transmembrane Precursor, Clac-P.Collagen Type XXV" Embo J., vol. 21, No. 7, 2002, pp. 1524-1534.
European Search Report (Dated Jun. 13, 2003).
Holschneider, D. P. et al., "Genotype to phenotytpe: Challenges and Opportunities" Int. J. Devl. Neuroscience 18 pp. 615-618, (2000).
Berg, J. et al., Johns Hopkins University School of Medicine, Some Pre-m RNA Molecules can be Spliced in Alternative Ways to Yield Different mRNAs, Biochemistry, Fifth Edition, W.H. Freeman and Company, New York, 2002, Table 28.3.6.
Wisnieski, T. et al. Neuroscience Letters "Apolipoprotein E: a pathological chaperone protein in patients with cerebral and systemic amyloid", vol. 135, p. 235-238 (1992).
Glenner, George G., M.D. et al. Biochemical Biophysical Research Communications, pp. 1131-1135, vol. 122, No. 3, Aug. 16, 1984, "Alzheimer's Disease and Down's Syndrome: Sharing a Unique Cerebrovascular Amyloid Fibril Protein".
Namba et al., Brain Research, 541 (1991) 163-166, "Apolipoprotein E immunoreativity in cerebral amyloid deposits and neurofibrillary tangles in Alzheimer's disease and kuru plaque amyloid in Creutzfeldt-Jakob disease".
Eikelenboom, P. and Stam, F.C.; Acta Neuropathol (Berl) (1982) 57:239-242, "Immunoglobulins and Complement Factors in Senile Plaques".
Ma, Jianyi et al., Letters to Nature, Amyloid-associated proteins a1-antichynitrtpsin and apolipoprotein E promote assembly of Alzheimer β-protein into filaments, vol. 372, Nov. 1994, pp. 92-97.
Webster, Scott et al., Journal of Neuroscience Research 46:58-66 (1996); "Rapid Communication, Relative Efficacies of Amyloid β Peptide (Aβ) Binding Proteins in Aβ Aggregation".
Yankner, Bruce et al., Science, vol. 250, "Neurotrophic and Neurotoxic Effects of Amyloid β Protein: Reversal of Tachykinin Neuropeptides", Oct. 12, 1990.
Yan, Shi Du, et al. Nature—vol. 382-22 Aug. 1996, "Rage and amyloid-β peptide neurotoxicity in Alzheimer's disease", pp. 685-691.
Irizarry, Michael C. et al., The Journal of Neuroscience, Sep. 15, 1997, 17(18); 7053-7059; "Aβ Deposition is Associated with Neuropil Changes, but not with Overt Neuronal Loss in the Human Amyloid Precursor Protein V717F (PDAPP) Transgenic Mouse".

(Continued)

*Primary Examiner* — Elizabeth C Kemmerer
*Assistant Examiner* — Kimberly A Ballard
(74) *Attorney, Agent, or Firm* — Studebaker & Brackett PC; Donald R. Studebaker

(57) ABSTRACT

A novel human collagen-like protein CLAC occurring in brain amyloid and its precursor CLAC-P; genes encoding the same; cDNA of mouse CLAC-P and its deduced amino acid sequence; antibodies specific to these proteins; and methods of diagnosing treating and preventing Alzheimer's disease by using the same.

5 Claims, 5 Drawing Sheets

OTHER PUBLICATIONS

Corder, E.H. et al., Science—vol. 261—Aug. 13, 1993, "Gene Dose of Apolipoprotein Type 4 Allele and the Risk of Alzheimer's Disease in late Onset Families", pp. 921-923.

Database Embl. Online!, EST, 388 bp Jun. 28, 1997, "aa94h07.r1 Stratagene fetal retina 937202 Homo sapiens cDNA clone, Image: 839005 5' similar to TR: G1054873 G1054873 Alpha-2 IX Collagen; mRNA sequence" Retrieved from EBI Database accession No. AA487419 XP002242636.

Burgess et al., J of Cell Bio., 111: 2129-2138 (1990).

Lazar et al., Mol. & Cell. Bio., 8: 1247-1252 (1998).

Meinkoth et al., Analytical Biochemistry, 138: 267-284 (1984).

Bowie et al., Science 247: 1306-1310 (1990).

Berg et al., Biochemistry, Fifth Edition, W.H. Freeman and Company, New York, 2002, Section #28.3.6 and Table 28.4.

Yuling, S. et al., The Journal of Neuroscience, "Glial Fibrillary Acidic Protein-Apolipoprotein E (apoE) Transgenic Mice: Astrocyte-Specific Expression and Differing . . . ",. vol. 18, pp. 3261-3272, (1998).

Thaian N. Ton; Final Office Action; U.S. Appl. No. 12/329,218; Jun. 4, 2010.

Thaian N. Ton; Non-Final Office Action; U.S. Appl. No. 12/329,218; Jan. 7, 2010.

* cited by examiner

Figure 1A

```
CCGCGACTTCGGCTTCGCGAGTAGCATTGGTTCCTTGGGTTTATTTCGTTTTCCTCTCTC    60
TTCTCCACCTTAGTCGCCCCTTTCGCGCTGCGCTGTAGCGTGCTCTCACAGCCTTTTTGC   120
CTTGAACTGAATGCAGGTGGGAAACAGGTCGGCGTGCCGAAAGACACCGAGTAGGTAGAA   180
ATAAGGCAAACTCACAGAGGCGCAACAGGTCCGGTCCTCCGTGGCCAGGGCGAGCCGCGG   240
CCCCGCGTGGCGCCTCGGCCGTTGCCCTCGGACCCTGAGCGGCCACTGTTGGGGCCCTCG   300
AAAGAGGTGTCGGTCCTCTGGGAGTCGGAAGAGCTGTCTGGGTGGGTTTCGTCTTGCTTT   360
TTACCCCACCGCCACCCAGTCCCCGGACGGAGGGTGCTTTTCACTTCCAGCTGGGAGGAG   420
AGAAGAAAGCGGGGATGGTGCACGCCTGCGGGTCTGGACGCTGAGCAAGGCAGGGGATTA   480
TTTGAGGTGTAGAGGGTGGGAAGCGAAGCCGAGACGGCCGACCCCGCCACGATGCTGCTG   540
                                              M  L  L
AAGAAGCACGCAGGGAAAGGAGGGGGCCGGGAGCCCAGATCCGAGGACCCGACCCCTGCC   600
 K  K  H  A  G  K  G  G  R  E  P  R  S  E  D  P  T  P  A
GAACAGCATTGTTCCCGGACCATGCCCCCGTGTGCCGTCCTGGCGGCCCTCCTGTCAGTG   660
 E  Q  H  C  S  R  T  M  P  P  C  A  V  L  A  A  L  L  S  V
GTGGCCGTGGTGTCTTGCCTGTACCTGGGTGTGAAAACCAACGACCTCCAGGCGAGGATC   720
 V  A  V  V  S  C  L  Y  L  G  V  K  T  N  D  L  Q  A  R  I
GCCGCTCTCGAATCCGCCAAAGGGGCCCCCTCCATTCATCTGCTGCCTGATACCCTGGAT   780
 A  A  L  E  S  A  K  G  A  P  S  I  H  L  L  P  D  T  L  D
CACCTCAAGACTATGGTGCAAGAGAAAGTGGAGCGACTTCTGGCTCAGAAATCCTATGAA   840
 H  L  K  T  M  V  Q  E  K  V  E  R  L  L  A  Q  K  S  Y  E
CATATGGCTAAAATAAGAATCGCAAGAGAAGCACCTTCAGAATGTAACTGCCCAGCAGGC   900
 H  M  A  K  I  R  I  A  R  E  A  P  S  E  C  N  C  P  A  G
CCTCCAGGGAAACGAGGTAAGAGAGGCCGAAGAGGAGAATCTGGTCCTCCTGGACAGCCT   960
 P  P  G  K  R  G  K  R  G  R  R  G  E  S  G  P  P  G  Q  P
GGTCCTCAGGGCCCTCCTGGTCCAAAAGGCGATAAGGGAGAACAAGGTGATCAGGGACCT  1020
 G  P  Q  G  P  P  G  P  K  G  D  K  G  E  Q  G  D  Q  G  P
AGGATGGTGTTTCCTAAAATCAATCATGGGTTTCTCTCTGCTGATCAGCAGCTCATTAAA  1080
 R  M  V  F  P  K  I  N  H  G  F  L  S  A  D  Q  Q  L  I  K
CGCCGCCTGATTAAGGGTGACCAAGGACAGGCAGGGCCTCCAGGACCCCCTGGCCCTCCA  1140
 R  R  L  I  K  G  D  Q  G  Q  A  G  P  P  G  P  P  G  P  P
GGCCCAAGAGGGCCACCTGGGGACACAGGGAAAGATGGCCCCCGTGGAATGCCAGGAGTA  1200
 G  P  R  G  P  P  G  D  T  G  K  D  G  P  R  G  M  P  G  V
CCCGGTGAACCAGGAAAGCCAGGAGAACAAGGCTTGATGGGTCCTCTAGGGCCTCCGGGA  1260
 P  G  E  P  G  K  P  G  E  Q  G  L  M  G  P  L  G  P  P  G
CAAAAGGGTTCTATTGGAGCACCTGGAATTCCAGGGATGAATGGGCAAAAGGGTGAGCCC  1320
 Q  K  G  S  I  G  A  P  G  I  P  G  M  N  G  Q  K  G  E  P
GGGTTGCCTGGAGCAGTAGGACAGAATGGAATACCAGGACCTAAGGGAGAACCTGGAGAA  1380
 G  L  P  G  A  V  G  Q  N  G  I  P  G  P  K  G  E  P  G  E
CAAGGTGAAAAGGGAGACGCTGGAGAGAACGGCCCCAAGGGTGACACAGGCGAAAAGGGT  1440
 Q  G  E  K  G  D  A  G  E  N  G  P  K  G  D  T  G  E  K  G
GACCCTGGATCATCTGCTGCAGGAATTAAGGGAGAACCTGGGGAATCTGGTCGTCCAGGG  1500
 D  P  G  S  S  A  A  G  I  K  G  E  P  G  E  S  G  R  P  G
```

Figure 1B

```
CAAAAGGGTGAACCAGGGCTTCCTGGGCTTCCTGGACTTCCGGGGATAAAGGGAGAACCA    1560
 Q  K  G  E  P  G  L  P  G  L  P  G  L  P  G  I  K  G  E  P
GGTTTCATTGGTCCTCAAGGAGAACCAGGCTTACCAGGTTTACCAGGAACAAAAGGTGAA    1620
 G  F  I  G  P  Q  G  E  P  G  L  P  G  L  P  G  T  K  G  E
CGGGGGGAAGCAGGGCCTCCTGGAAGAGGTGAGCGAGGGGAACCTGGAGCCCCCGGACCA    1680
 R  G  E  A  G  P  P  G  R  G  E  R  G  E  P  G  A  P  G  P
AAGGGGAAACAAGGTGAATCAGGAACTAGAGGCCCAAAGGGGTCAAAGGGGGATCGTGGA    1740
 K  G  K  Q  G  E  S  G  T  R  G  P  K  G  S  K  G  D  R  G
GAAAAAGGGGACTCTGGAGCTCAGGGACCAAGGGGTCCACCTGGTCAAAAGGGGATCAA    1800
 E  K  G  D  S  G  A  Q  G  P  R  G  P  P  G  Q  K  G  D  Q
GGAGCCACTAAGATCATAGACTACAACGGCAACCTCCACGAAGCCTTACAGAGGATTACC    1860
 G  A  T  K  I  I  D  Y  N  G  N  L  H  E  A  L  Q  R  I  T
ACCTTAACTGTCACGGGTCCCCCTGGACCTCCTGGACCTCAAGGACTACAAGGGCCAAAG    1920
 T  L  T  V  T  G  P  P  G  P  P  G  P  Q  G  L  Q  G  P  K
GGAGAGCAGGGATCTCCAGGAATCCCAGGAATGGATGGAGAGCAGGGACTCAAAGGCTCA    1980
 G  E  Q  G  S  P  G  I  P  G  M  D  G  E  Q  G  L  K  G  S
AAGGGAGACATGGGGGACCCAGGTATGACAGGTGAAAAAGGAGGAATTGGACTTCCTGGA    2040
 K  G  D  M  G  D  P  G  M  T  G  E  K  G  G  I  G  L  P  G
TTACCGGGAGCCAATGGAATGAAAGGAGAAAAAGGAGATTCTGGAATGCCGGGTCCACAG    2100
 L  P  G  A  N  G  M  K  G  E  K  G  D  S  G  M  P  G  P  Q
GGTCCTTCTATCATAGGCCCCACCAGGCCCACCAGGTCCCCATGGCCCACCTGGCCCCATG    2160
 G  P  S  I  I  G  P  P  G  P  P  G  P  H  G  P  P  G  P  M
GGACCTCATGGACTTCCTGGACCAAAGGGTACAGATGGTCCTATGGGACCCCATGGCCCT    2220
 G  P  H  G  L  P  G  P  K  G  T  D  G  P  M  G  P  H  G  P
GCAGGTCCCAAAGGAGAAAGAGGTGAAAAAGGAGCTATGGGAGAGCCTGGACCAAGAGGG    2280
 A  G  P  K  G  E  R  G  E  K  G  A  M  G  E  P  G  P  R  G
CCCTATGGGCTGCCT GGGAAAGATGGAGAGCCTGGTCTTGAT GGCTTCCCTGGTCCACGG    2340
 P  Y  G  L  P  G  K  D  G  E  P  G  L  D  G  F  P  G  P  R
GGTGAGAAGGGTGATCTAGGAGAAAAGGGAGAAAAG GGATTCCGTGGCGTTAAGGGGGAA    2400
 G  E  K  G  D  L  G  E  K  G  E  K  G  F  R  G  V  K  G  E
 AAAGGGGAGCCAGGCCAGCCTGGCCTGGATGGGCTGGATGCCCCTTGCCAATTG GGGCCA   2460
 K  G  E  P  G  Q  P  G  L  D  G  L  D  A  P  C  Q  L  G  P
GATGGCTTACCCATGCCTGGCTGTTGGCAAAAGTGATGAATCTAACCTTTCAAGCATGAA    2520
 D  G  L  P  M  P  G  C  W  Q  K  *
GTTGTGTATATAAGGGTCCATTTTTAATATTTATAGTTGAAAACTGAATTGCAGATTTTA    2580
CAAGTCTGAGATATGTTTACATAGGGC                                     2607
```

     Kozak sequence

     Sequence expected to undergo alternative splicing

HEK293 cells permanently expressing CLAC-P

CLAC-P permanently expressed in HEK293 cells
A   Immunostaining image of HEK293 cells expressing CLAC-P
B   Western blot of HEK293 cell membrane fraction expressing CLAC-P

Figure 3

SEQ ID NO. : 4 8
CCCGGCGCCACACAGTCCCCGGCCGGAGGGTGCTTTTCACTCCTAGCTGGAAGGGGAGA
AAGAATCTGGAGGACGGTCGGTCCACGCCTGCTGATCCGGACGCCGAGCCACGCGCAGG
TCCATCTCTAAGCCCGGGCTCCGACTCTACCAACTAGTTGTGCAGCCGCAGGGACTGAA
CTTTGGAGGAACCGACCCTTCCTCTCATTCTAAGATTACTGGAGGAGATAGAAGGTGGA
AGGCGTAGCGGAGGCCAGCGACCCCGCCACAATGTTGGTGAAGAAGCTTGCAGGGAAAG
GAGGGGGACGAGAGTCTGGATCAGAAGATCCGCGCCCTTGGGACAGCGTTGTGCCGGC
ACCATGCCCTCGTGCACGGCCCTGGCGACCCTCTTGTCAGTGGTTGCTGTGGCTTTCTG
TTTTTATCTTGGGGTGAAAACCAACGACCTCCAGGCGAGGATTGTTGCTCTTGAATCTG
CTAAAGGGACCCCTTCCTTCCATCCGCTGTCTGACACCGTGGATGAGCTGAAGGCAATG
GTTCAGGAGAAAGTGGAGCGTCTCTTGGCTCAGAAATCCTACGAATATATGGCTAAAAT
AAGAACGGTCAGGGAGGCACCTTTAGAGTGCAACTGCCCAGCAGGTCCTCCAGGGAAAC
GAGGGAAGAGAGGCCGAAGAGGAGAATCTGGTCCTCCTGGTCAGCCTGGTCCTCAGGGC
CCTCCTGGTCCAAAAGGTGATAAGGGAGAACAAGGTGATCAGGGACCTCGGATGGTGTT
TCCTAAAATCAATCACGGCTTTCTCTCTGCTGATCAGCAGCTCATTAAACGCCGGCTGA
TTAAGGGTGACCAAGGACAGGCAGGGCCTCCAGGACCTCCAGGCCCTCCTGGTCCAAGA
GGCCCACCTGGGGACACAGGAAAGGACGGCCCCGAGGAATGCCAGGAGTACCTGGTGA
ACCAGGAAAACCAGGAGAACAAGGCTTGATGGGACCTCTGGGCCTCCAGGACAAAAGG
GTTCCATTGGAGCACCTGGGACCCCAGGCATGGATGGGCAAAAGGGTGAGCCTGGATCA
CCTGGAGCAGCCGGGCAGAGTGGACTACCAGGACCTAAGGGAGAACCTGGAAAAGAAGG
AGAAAGGGAGATGCTGGAGAAAATGGTCCCAAAGGTGATACAGGAGAAAAGGGTGACC
CTGGATCATCTGCTGCAGGAATTAAGGGAGAACCTGGAGAATCTGGCCGCCCGGGGCAG
AAGGGTGAACCAGGGCTGCCTGGGCTGCCTGGACTTCCGGGAATAAAGGGAGAACCAGG
CTTCATTGGTCCTCAAGGAGAACCAGGGTTACCAGGGCTACCAGGAACAAAAGGTGATC
GTGGGGAGGCGGGGCCTCCTGGAAGAGGTGAACGAGGAGATCCTGGAGCCCCGGGGCCA
AAGGGGAAGCAAGGTGAATCAGGAGCTAGAGGCCCGAAGGGGTCAAAGGGTGATCGTGG
AGACAAAGGAGACTCTGGCGCTCTGGGACCACGGGTCCACCTGGACAAAAGGGGGATC
CAGGAGCCACAGAGATCATAGACTACAATGGCAACCTCCATGAGGCCTTACAGAGAATT
ACCACCTTAACTGTCACGGGCCCCCCTGGACCTCCTGGACCTCAAGGACTACAAGGGCC
AAAGGGTGAGCAAGGCTCTCCAGGAATCCCCGGAGTTGATGGAGAACAGGGACTCAAAG
GCTCCAAGGGAGACATGGGGGACCCAGGTGTGCAGGTGAAAAAGGAGGACTGGGACTT
CCTGGATTGCCGGGTGCCAATGGAGTAAAAGGAGAGAAAGGAGACACCGGTTTGCCAGG
TCCTCAGGGGCCTTCTATCATAGGCCCACCAGGCCCTCCAGGTCCCCATGGCCCACCTG
GTCCCATGGGCCCCATGGACTTCCTGGACCAAAGGGAGCATCTGGCTTAGACGGAAAG
CCAGGATCCCGGGGTGCAGATGGTCCTATAGGACCCCACGGCCCTGCAGGACCCAAAGG
AGAAAGAGGAGAGAAAGGAGCTATGGGAGAGCCTGGACCCAGAGGGCCCTATGGGCTGC
CTGGCAAAGATGGAGAACCTGGTCTTGATGGCTTCCCTGGTCCTCGAGGCGAGAAGGGT
GACCTGGGAGAAAAGGGAGAAAAGGGATTCCGTGGCGTTAAGGGGGAAAAGGGGAGCC
AGGCCAGCCTGGCCTGGATGGGCTGGATGCTCCTTGCCAATTGGGACCTGATGGGTTAC
CTATGCCTGGCTGCTGGCAAAAGTGATGAATCTAACCTTCCGAGCATGAAGTTGTG

Figure 4

SEQ ID NO.: 4 9
MLVKKLAGKGGGRESGSEDPRPLGQRCAGTMPSCTALATLLSVVAVAFCFYLGVKTND
LQARIVALESAKGTPSFHPLSDTVDELKAMVQEKVERLLAQKSYEYMAKIRTVREAPL
ECNCPAGPPGKRGKRGRRGESGPPGQPGPQGPPGPKGDKGEQGDQGPRMVFPKINHGF
LSADQQLIKRRLIKGDQGQAGPPGPPGPPGPRGPPGDTGKDGPRGMPGVPGEPGKPGE
QGLMGPLGPPGQKGSIGAPGTPGMDGQKGEPGSPGAAGQSGLPGPKGEPGKEGEKGDA
GENGPKGDTGEKGDPGSSAAGIKGEPGESGRPGQK<u>GEPGLPGLPGLPGI</u>KGEPGFIGP
QGEPGLPGLPGTKGDRGEAGPPGRGERGDPGAPGPKGKQGESGARGPKGSKGDRGDKG
DSGALGPRGPPGQKGDPGATEIIDYNGNLHEALQRITTLTVTGPPGPPGPQGLQGPKG
EQGSPGIPGVDGEQGLKGSKGDMGDPGVPGEKGGLGLPGLPGANGVKGEKGDTGLPGP
QGPSIIGPPGPPGPHGPPGPMGPHGLPGPKGASGLDGKPGSRGADGPIGPHGPAGPKG
ERGEKGAMGEPGPRGPYGLPGKDGEPGLDGFPGPRGEKGDLGEKGEKGFRGVKGEKGE
PGQPGLDGLDAPCQLGPDGLPMPGCWQK

```
                          SEQUENCE LISTING

<160> NUMBER OF SEQ ID NOS: 56

<210> SEQ ID NO 1
<211> LENGTH: 2607
<212> TYPE: DNA
<213> ORGANISM: Homo sapiens

<400> SEQUENCE: 1
ccgcgacttc ggcttcgcga gtagcattgg ttccttgggt ttatttcgtt ttcctctctc      60
ttctccacct tagtcgcccc tttcgcgctg cgctgtagcg tgctctcaca gccttttttgc    120 cttgaactga atgcaggtgg gaaacaggtc ggcgtgccga agacaccga gtaggtagaa      180 ataaggcaaa ctcacagagg cgcaacaggt ccggtcctcc gtgccaggg cgagccgcgg     240 ccccgcgtgg cgcctcggcc gttgccctcg accctgagc ggccactgtt ggggccctcg     300
aaagaggtgt cggtcctctg ggagtcggaa gagctgtctg ggtgggtttc gtcttgctttt   360 ttaccccacc gccacccagt ccccggacgg agggtgcttt tcacttccag ctgggaggag    420
agaagaaagc ggggatggtg cacgcctgcg ggtctggacg ctgagcaagg caggggatta    480
tttgaggtgt agagggtggg aagcgaagcc gagacggccg accccgccac gatgctgctg    540
aagaagcacg cagggaaagg aggggggccgg gagcccagat ccgaggaccc gaccctgcc    600 cagcagcatt gttcccggac catgcccccg tgtgccgtcc tggcggccct cctgtcagtg    660
gtggccgtgg tgtcttgcct gtacctgggt gtgaaaacca acgacctcca ggcgaggatc    720
gccgctctcg aatccgccaa aggggccccc tccattcatc tgctgcctga taccctggat    780
cacctcaaga ctatggtgca agagaaagtg agcgacttc tggctcagaa atcctatgaa    840
catatggcta aaataagaat cgcaagagaa gcaccttcag aatgtaactg cccagcaggc    900
cctccaggga acgaggtaa gagaggccga agaggagaat ctggtcctcc tggacagcct    960
ggtcctcagg gccctcctgg tccaaaaggc gataagggag aacaaggtga tcagggacct   1020
aggatggtgt tcctaaaat caatcatggg tttctctctg ctgatcagca gctcattaaa    1080
cgccgcctga ttaagggtga ccaaggacag gcagggcctc caggaccccc tggccctcca   1140
ggcccaagag ggcacctgg ggacacaggg aaagatggcc ccgtggaat gccaggagta    1200 cccggtgaac caggaaagc aggagaacaa ggcttgatgg gtcctctagg gcctccggga   1260
caaaagggtt ctattggagc acctggaatt ccagggatga atgggcaaaa gggtgagccc   1320
gggttgcctg gagcagtagg acagaatgga ataccaggac ctaaggagga acctggagaa   1380
```

```
caaggtgaaa agggagacgc tggagagaac ggccccaagg gtgacacagg cgaaaagggt    1440
gaccctggat catctgctgc aggaattaag ggagaacctg gggaatctgg tcgtccaggg    1500
caaaagggtg aaccagggct tcctgggctt cctggacttc cggggataaa gggagaacca    1560
ggtttcattg gtcctcaagg agaaccaggc ttaccaggtt taccaggaac aaaaggtgaa    1620
cgggggaag caggcctcc tggaagaggt gagcgagggg aacctggagc cccggacca       1680
aaggggaaac aaggtgaatc aggaactaga ggcccaaagg ggtcaaaggg ggatcgtgga    1740
gaaaagggg actctggagc tcagggacca aggggtccac ctggtcaaaa aggggatcaa     1800
ggagccacta agatcataga ctacaacggc aacctccacg aagccttaca gaggattacc    1860
accttaactg tcacgggtcc ccctggacct cctggacctc aaggactaca agggccaaag    1920
ggagagcagg gatctccagg aatcccagga atggatggag agcagggact caaaggctca    1980
aagggagaca tgggggaccc aggtatgaca ggtgaaaaag gaggaattgg acttcctgga    2040
ttaccgggag ccaatggaat gaaaggagaa aaggagagatt ctggaatgcc gggtccacag   2100
ggtccttcta tcataggccc accaggccca ccaggtcccc atggcccacc tggccccatg    2160
ggacctcatg gacttcctgg accaaagggt acagatggtc ctatgggacc ccatggcct    2220
gcaggtccca aggagaaag aggtgaaaaa ggagctatgg gagagcctgg accaagaggg    2280
ccctatgggc tgcctgggaa agatggagag cctggtcttg atggcttccc tggtccacgg    2340
ggtgagaagg gtgatctagg agaaaaggga gaaagggat tccgtggcgt taagggggaa    2400
aaaggggagc caggccagcc tggcctggat gggctgatg ccccttgcca attgggccca    2460
gatggcttac ccatgcctgg ctgttggcaa aagtgatgaa tctaaccttt caagcatgaa    2520
gttgtgtata aagggtccca ttttttaatat ttatagttga aaactgaatt gcagattta     2580
caagtctgag atatgtttac ataggc                                          2607
```

<210> SEQ ID NO 2
<211> LENGTH: 654
<212> TYPE: PRT
<213> ORGANISM: Homo sapiens

<400> SEQUENCE: 2

```
Met Leu Leu Lys Lys His Ala Gly Lys Gly Gly Arg Glu Pro Arg
1               5                   10                  15

Ser Glu Asp Pro Thr Pro Ala Glu Gln His Cys Ser Arg Thr Met Pro
            20                  25                  30

Pro Cys Ala Val Leu Ala Ala Leu Leu Ser Val Val Ala Val Val Ser
        35                  40                  45

Cys Leu Tyr Leu Gly Val Lys Thr Asn Asp Leu Gln Ala Arg Ile Ala
    50                  55                  60

Ala Leu Glu Ser Ala Lys Gly Ala Pro Ser Ile His Leu Leu Pro Asp
65                  70                  75                  80

Thr Leu Asp His Leu Lys Thr Met Val Gln Glu Lys Val Glu Arg Leu
                85                  90                  95

Leu Ala Gln Lys Ser Tyr Glu His Met Ala Lys Ile Arg Ile Ala Arg
            100                 105                 110

Glu Ala Pro Ser Glu Cys Asn Cys Pro Ala Gly Pro Pro Gly Lys Arg
        115                 120                 125

Gly Lys Arg Gly Arg Gly Glu Ser Gly Pro Gly Gln Pro Gly
    130                 135                 140

Pro Gln Gly Pro Pro Gly Pro Lys Gly Asp Lys Gly Glu Gln Gly Asp
145                 150                 155                 160
```

```
-continued

Gln Gly Pro Arg Met Val Phe Pro Lys Ile Asn His Gly Phe Leu Ser
                165                 170                 175

Ala Asp Gln Gln Leu Ile Lys Arg Arg Leu Ile Lys Gly Asp Gln Gly
            180                 185                 190

Gln Ala Gly Pro Pro Gly Pro Pro Gly Pro Pro Gly Pro Arg Gly Pro
        195                 200                 205

Pro Gly Asp Thr Gly Lys Asp Gly Pro Arg Gly Met Pro Gly Val Pro
    210                 215                 220

Gly Glu Pro Gly Lys Pro Gly Glu Gln Gly Leu Met Gly Pro Leu Gly
225                 230                 235                 240

Pro Pro Gly Gln Lys Gly Ser Ile Gly Ala Pro Gly Ile Pro Gly Met
            245                 250                 255

Asn Gly Gln Lys Gly Glu Pro Gly Leu Pro Gly Ala Val Gly Gln Asn
        260                 265                 270

Gly Ile Pro Gly Pro Lys Gly Glu Pro Gly Glu Gln Gly Glu Lys Gly
    275                 280                 285

Asp Ala Gly Glu Asn Gly Pro Lys Gly Asp Thr Gly Glu Lys Gly Asp
        290                 295                 300

Pro Gly Ser Ser Ala Ala Gly Ile Lys Gly Glu Pro Gly Glu Ser Gly
305                 310                 315                 320

Arg Pro Gly Gln Lys Gly Glu Pro Gly Leu Pro Gly Leu Pro Gly Leu
            325                 330                 335

Pro Gly Ile Lys Gly Glu Pro Gly Phe Ile Gly Pro Gln Gly Glu Pro
        340                 345                 350

Gly Leu Pro Gly Leu Pro Gly Thr Lys Gly Glu Arg Gly Glu Ala Gly
    355                 360                 365

Pro Pro Gly Arg Gly Glu Arg Gly Glu Pro Gly Ala Pro Gly Pro Lys
370                 375                 380

Gly Lys Gln Gly Glu Ser Gly Thr Arg Gly Pro Lys Gly Ser Lys Gly
385                 390                 395                 400

Asp Arg Gly Glu Lys Gly Asp Ser Gly Ala Gln Gly Pro Arg Gly Pro
            405                 410                 415

Pro Gly Gln Lys Gly Asp Gln Gly Ala Thr Lys Ile Ile Asp Tyr Asn
        420                 425                 430

Gly Asn Leu His Glu Ala Leu Gln Arg Ile Thr Thr Leu Thr Val Thr
    435                 440                 445

Gly Pro Pro Gly Pro Pro Gly Pro Gln Gly Leu Gln Gly Pro Lys Gly
    450                 455                 460

Glu Gln Gly Ser Pro Gly Ile Pro Gly Met Asp Gly Glu Gln Gly Leu
465                 470                 475                 480

Lys Gly Ser Lys Gly Asp Met Gly Asp Pro Gly Met Thr Gly Glu Lys
            485                 490                 495

Gly Gly Ile Gly Leu Pro Gly Leu Pro Gly Ala Asn Gly Met Lys Gly
        500                 505                 510

Glu Lys Gly Asp Ser Gly Met Pro Gly Pro Gln Gly Pro Ser Ile Ile
    515                 520                 525

Gly Pro Pro Gly Pro Pro Gly Pro His Gly Pro Pro Gly Pro Met Gly
    530                 535                 540

Pro His Gly Leu Pro Gly Pro Lys Gly Thr Asp Gly Pro Met Gly Pro
545                 550                 555                 560

His Gly Pro Ala Gly Pro Lys Gly Glu Arg Gly Glu Lys Gly Ala Met
            565                 570                 575

Gly Glu Pro Gly Pro Arg Gly Pro Tyr Gly Leu Pro Gly Lys Asp Gly
        580                 585                 590
```

```
Glu Pro Gly Leu Asp Gly Phe Pro Gly Pro Arg Gly Glu Lys Gly Asp
            595                 600                 605

Leu Gly Glu Lys Gly Glu Lys Gly Phe Arg Gly Val Lys Gly Glu Lys
        610                 615                 620

Gly Glu Pro Gly Gln Pro Gly Leu Asp Gly Leu Asp Ala Pro Cys Gln
625                 630                 635                 640

Leu Gly Pro Asp Gly Leu Pro Met Pro Gly Cys Trp Gln Lys
                645                 650

<210> SEQ ID NO 3
<211> LENGTH: 14
<212> TYPE: PRT
<213> ORGANISM: Homo sapiens

<400> SEQUENCE: 3

Glu Pro Arg Ser Glu Asp Pro Thr Pro Ala Glu Gln His Cys
1               5                   10

<210> SEQ ID NO 4
<211> LENGTH: 15
<212> TYPE: PRT
<213> ORGANISM: Artificial
<220> FEATURE:
<223> OTHER INFORMATION: NC2-1 peptide

<400> SEQUENCE: 4

Gly Cys Asn His Gly Phe Leu Ser Ala Asp Gln Gln Leu Ile Lys
1               5                   10                  15

<210> SEQ ID NO 5
<211> LENGTH: 16
<212> TYPE: PRT
<213> ORGANISM: Artificial
<220> FEATURE:
<223> OTHER INFORMATION: NC2-2
<220> FEATURE:
<221> NAME/KEY: MISC_FEATURE
<222> LOCATION: (15)..(15)
<223> OTHER INFORMATION: Xaa at position 15 is hydroxyproline

<400> SEQUENCE: 5

Cys Lys Gly Glu Gln Gly Asp Gln Gly Pro Arg Met Val Phe Xaa Lys
1               5                   10                  15

<210> SEQ ID NO 6
<211> LENGTH: 15
<212> TYPE: PRT
<213> ORGANISM: Artificial
<220> FEATURE:
<223> OTHER INFORMATION: NC3 peptide

<400> SEQUENCE: 6

Asp Tyr Asn Gly Asn Leu His Glu Ala Leu Gln Arg Ile Thr Cys
1               5                   10                  15

<210> SEQ ID NO 7
<211> LENGTH: 14
<212> TYPE: PRT
<213> ORGANISM: Homo sapiens

<400> SEQUENCE: 7

Leu Gly Pro Asp Gly Leu Pro Met Pro Gly Cys Trp Gln Lys
1               5                   10

<210> SEQ ID NO 8
```

```
<211> LENGTH: 14
<212> TYPE: PRT
<213> ORGANISM: Homo sapiens

<400> SEQUENCE: 8

Ile Asn His Gly Phe Leu Ser Ala Asp Gln Gln Leu Ile Lys
1               5                   10

<210> SEQ ID NO 9
<211> LENGTH: 14
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is hydroxyproline

<400> SEQUENCE: 9

Gly Glu Gln Gly Asp Gln Gly Xaa Arg Met Val Phe Pro Lys
1               5                   10

<210> SEQ ID NO 10
<211> LENGTH: 18
<212> TYPE: PRT
<213> ORGANISM: Homo sapiens

<400> SEQUENCE: 10

Asp Gln Gly Pro Arg Met Val Phe Pro Lys Ile Asn His Gly Phe Leu
1               5                   10                  15

Ser Ala

<210> SEQ ID NO 11
<211> LENGTH: 28
<212> TYPE: PRT
<213> ORGANISM: Homo sapiens

<400> SEQUENCE: 11

Gly Glu Gln Gly Asp Gln Gly Pro Arg Met Val Phe Pro Lys Ile Asn
1               5                   10                  15

His Gly Phe Leu Ser Ala Asp Gln Gln Leu Ile Lys
            20                  25

<210> SEQ ID NO 12
<211> LENGTH: 26
<212> TYPE: DNA
<213> ORGANISM: Artificial
<220> FEATURE:
<223> OTHER INFORMATION: designed oligonucleotide primer to amplify
      human CLAC-P cDNA fragment
<220> FEATURE:
<221> NAME/KEY: misc_feature
<222> LOCATION: (6)..(6)
<223> OTHER INFORMATION: n at position 6 is inosine
<220> FEATURE:
<221> NAME/KEY: misc_feature
<222> LOCATION: (15)..(15)
<223> OTHER INFORMATION: n at position 15 is inosine
<220> FEATURE:
<221> NAME/KEY: misc_feature
<222> LOCATION: (24)..(24)
<223> OTHER INFORMATION: n at position 24 is inosine

<400> SEQUENCE: 12
aarggngarc arggngayca rggncc                                              26

<210> SEQ ID NO 13
<211> LENGTH: 26
<212> TYPE: DNA
```

<213> ORGANISM: Artificial
<220> FEATURE:
<223> OTHER INFORMATION: designed oligonucleotide primer to amplify
      human CLAC-P cDNA fragment
<220> FEATURE:
<221> NAME/KEY: misc_feature
<222> LOCATION: (12)..(12)
<223> OTHER INFORMATION: n at position 12 is inosine

<400> SEQUENCE: 13
agctgctgrt cngcdgavag raabcc                                          26

<210> SEQ ID NO 14
<211> LENGTH: 26
<212> TYPE: DNA
<213> ORGANISM: Artificial
<220> FEATURE:
<223> OTHER INFORMATION: designed oligonucleotide primer to amplify
      human CLAC-P cDNA fragment
<220> FEATURE:
<221> NAME/KEY: misc_feature
<222> LOCATION: (12)..(12)
<223> OTHER INFORMATION: n at position 12 is inosine

<400> SEQUENCE: 14
agctgctgrt cngcrctvag raabcc                                          26

<210> SEQ ID NO 15
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 15
tagctgctgg tcggcgctga ggaagcca                                        28

<210> SEQ ID NO 16
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 16 aaggggggaac aggggggacca ggggccga                                      28

<210> SEQ ID NO 17
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 17
tcggaaacac catcctcggc ccctggtc                                        28

<210> SEQ ID NO 18
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 18

```
catggcttcc tcagcgccga ccagcagc                                              28
```

<210> SEQ ID NO 19
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 19

```
cgccgcctga ttaagggtga ccaaggac                                              28
```

<210> SEQ ID NO 20
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 20

```
aagagggcca cctggggaca cagggaaa                                              28
```

<210> SEQ ID NO 21
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 21

```
acccttgggg ccgttctctc cagcgtct                                              28
```

<210> SEQ ID NO 22
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 22

```
caccttgttc tccaggttct cccttagg                                              28
```

<210> SEQ ID NO 23
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 23

```
gaataccagg acctaaggga gaacctgg                                              28
```

<210> SEQ ID NO 24
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 24

```
ggccccaagg gtgacacagg cgaaaagg                                              28
```

-continued

```
<210> SEQ ID NO 25
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 25
ccctcctttc cctgcgtgct tcttcagc                                          28

<210> SEQ ID NO 26
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 26
tctcggcttc gcttcccacc ctctacac                                          28

<210> SEQ ID NO 27
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 27
ggagattctg gaatgccggg tccacagg                                          28

<210> SEQ ID NO 28
<211> LENGTH: 28
<212> TYPE: DNA
<213> ORGANISM: Artificial
<220> FEATURE:
<223> OTHER INFORMATION: designed oligonucleotide primer to amplify
      human CLAC-P cDNA fragment

<400> SEQUENCE: 28
cttctatcat aggcccacca ggcccacc                                          28

<210> SEQ ID NO 29
<211> LENGTH: 6
<212> TYPE: PRT
<213> ORGANISM: Artificial
<220> FEATURE:
<223> OTHER INFORMATION: designed to produce antibody Pyrog
<220> FEATURE:
<221> NAME/KEY: MISC_FEATURE
<222> LOCATION: (1)..(1)
<223> OTHER INFORMATION: Xaa at position 1 is pyroglutamic acid

<400> SEQUENCE: 29

Xaa Ala Pro Ser Glu Cys
1               5

<210> SEQ ID NO 30
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 30
```

```
gggatcaagg agccactaag atcataga                                          28
```

<210> SEQ ID NO 31
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 31

```
gggcctatga tagaaggacc ctgtggac                                          28
```

<210> SEQ ID NO 32
<211> LENGTH: 27
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 32

```
ctacaacggc aacctccacg aagcctt                                           27
```

<210> SEQ ID NO 33
<211> LENGTH: 22
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 33

```
tctccctttta tccccggaag tc                                               22
```

<210> SEQ ID NO 34
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 34

```
cgaatatatg gctaaaataa gaacggtc                                          28
```

<210> SEQ ID NO 35
<211> LENGTH: 27
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 35

```
ctggcaaacc ggtgtctcct ttctctc                                           27
```

<210> SEQ ID NO 36
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 36

```
acggtcaggg aggcaccttt agagtgca                                          28
```

```
<210> SEQ ID NO 37
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 37
ctctcctttt actccattgg cacccggc                                          28

<210> SEQ ID NO 38
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 38
acggtcaggg aggaagcttt agagtgca                                          28

<210> SEQ ID NO 39
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 39
tcaactccgg ggatccctgg agagcctt                                          28

<210> SEQ ID NO 40
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 40
gggaccattt tctcgagcat ctcccttt                                          28

<210> SEQ ID NO 41
<211> LENGTH: 27
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 41
aaaatggtcc caaaggtgat acaggag                                           27

<210> SEQ ID NO 42
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 42
tgcactctaa aggtgcctcc ctgaccgt                                          28

<210> SEQ ID NO 43
```

```
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 43
gaccgttctt attttagcca tatattcg                                              28

<210> SEQ ID NO 44
<211> LENGTH: 28
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 44
tggtaacctc catgaggcct tacagaga                                              28

<210> SEQ ID NO 45
<211> LENGTH: 27
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 45
gagagaaagg agacaccggt ttgccag                                               27

<210> SEQ ID NO 46
<211> LENGTH: 26
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 46
ggctggatgc tccttgccaa ttggga                                                26

<210> SEQ ID NO 47
<211> LENGTH: 27
<212> TYPE: DNA
<213> ORGANISM: Artificial
<220> FEATURE:
<223> OTHER INFORMATION: designed oligonucleotide primer to amplify
      mouse CLAC-P cDNA fragment

<400> SEQUENCE: 47
tgggacctga tgggttacct atgcctg                                               27

<210> SEQ ID NO 48
<211> LENGTH: 2298
<212> TYPE: DNA
<213> ORGANISM: Mus musculus

<400> SEQUENCE: 48
cccggcgcca cacagtcccc ggccggaggg tgcttttcac tcctagctgg aaggggagaa           60
agaatctgga ggacggtcgg tccacgcctg ctgatccgga cgccgagcca cgcgcaggtc          120
catctctaag cccgggctcc gactctacca actagttgtg cagccgcagg gactgaactt          180
tggaggaacc gacccttcct ctcattctaa gattactgga ggagatagaa ggtgaaggc           240 gtagcggagg ccagcgaccc cgccacaatg ttggtgaaga agcttgcagg gaaaggaggg          300
```

```
ggacgagagt ctggatcaga agatccgcgc cccttgggac agcgttgtgc cggcaccatg    360
ccctcgtgca cggccctggc gaccctcttg tcagtggttg ctgtggcttt ctgtttttat    420
cttggggtga aaccaacga cctccaggcg aggattgttg ctcttgaatc tgctaaaggg    480 acccccttcct tccatccgct gtctgacacc gtggatgagc tgaaggcaat ggttcaggag    540
aaagtggagc gtctcttggc tcagaaatcc tacgaatata tggctaaaat aagaacggtc    600
agggaggcac ctttagagtg caactgccca gcaggtcctc cagggaaacg agggaagaga    660
ggccgaagag gagaatctgg tcctcctggt cagcctggtc ctcagggccc tcctggtcca    720
aaaggtgata agggagaaca aggtgatcag ggacctcgga tggtgttttcc taaaatcaat    780 cacggctttc tctctgctga tcagcagctc attaaacgcc ggctgattaa gggtgaccaa    840
ggacaggcag ggcctccagg acctccaggc cctcctggtc aagaggccc acctggggac    900 acaggaaagg acggcccccg aggaatgcca ggagtacctg gtgaaccagg aaaaccagga    960
gaacaaggct tgatgggacc tctggggcct ccaggacaaa agggttccat ggagcacct    1020 gggaccccag gcatggatgg gcaaaagggt gagcctggat cacctggagc agccgggcag    1080
agtggactac caggacctaa gggagaacct ggaaaagaag gagaaagggg agatgctgga    1140
gaaaatggtc ccaaaggtga tacaggagaa agggtgacc ctggatcatc tgctgcagga    1200 attaaggggag aacctggaga atctggccgc cggggcaga agggtgaacc agggctgcct    1260
gggctgcctg gacttccggg aataaaggga gaaccaggct tcattggtcc tcaaggagaa    1320
ccagggttac cagggctacc aggaacaaaa ggtgatcgtg gggaggcggg gcctcctgga    1380
agaggtgaac gaggagatcc tggagccccg ggccaaagg ggaagcaagg tgaatcagga    1440
gctagaggcc cgaaggggtc aaaggtgat cgtggagaca aggagactc tggcgctctg    1500 ggaccacggg gtccacctgg acaaaagggg gatccaggag ccacagagat catagactac    1560
aatggcaacc tccatgaggc cttacagaga attaccacct taactgtcac gggccccct    1620 ggacctcctg gacctcaagg actacaaggg ccaaggggtg agcaaggctc tccaggaatc    1680 cccgagttg atggagaaca gggactcaaa ggctccaagg gagacatggg gacccaggt    1740 gtgccaggtg aaaaaggagg actgggactt cctggattgc cgggtgccaa tggagtaaaa    1800
ggagagaaag gagacaccgg tttgccaggt cctcaggggc cttctatcat aggcccacca    1860
ggccctccag gtcccatgg cccacctggt cccatgggg cccatggact tctggacca    1920 aagggagcat ctggcttaga cggaaagcca ggatcccggg gtgcagatgg tcctataggga    1980 ccccacggcc ctgcaggacc caaaggagaa agaggagaga aaggagctat gggagagcct    2040
ggacccagag ggccctatgg gctgcctggc aaagatggag aacctggtct tgatggcttc    2100
cctggtcctc gaggcgagaa gggtgacctg ggagaaaagg gagaaaaggg attccgtggc    2160 gttaagggggg aaaaggggga gccaggccag cctggcctgg atgggctgga tgctccttgc    2220
caattgggac ctgatgggtt acctatgcct ggctgctggc aaaagtgatg aatctaacct    2280
tccgagcatg aagttgtg                                                 2298
```

<210> SEQ ID NO 49
<211> LENGTH: 666
<212> TYPE: PRT
<213> ORGANISM: Mus musculus

<400> SEQUENCE: 49

```
Met Leu Val Lys Lys Leu Ala Gly Lys Gly Gly Gly Arg Glu Ser Gly
 1               5                  10                  15
```

```
Ser Glu Asp Pro Arg Pro Leu Gly Gln Arg Cys Ala Gly Thr Met Pro
            20                  25                  30

Ser Cys Thr Ala Leu Ala Thr Leu Leu Ser Val Val Ala Val Ala Phe
        35                  40                  45

Cys Phe Tyr Leu Gly Val Lys Thr Asn Asp Leu Gln Ala Arg Ile Val
    50                  55                  60

Ala Leu Glu Ser Ala Lys Gly Thr Pro Ser Phe His Pro Leu Ser Asp
65                  70                  75                  80

Thr Val Asp Glu Leu Lys Ala Met Val Gln Glu Lys Val Glu Arg Leu
                85                  90                  95

Leu Ala Gln Lys Ser Tyr Glu Tyr Met Ala Lys Ile Arg Thr Val Arg
            100                 105                 110

Glu Ala Pro Leu Glu Cys Asn Cys Pro Ala Gly Pro Pro Gly Lys Arg
        115                 120                 125

Gly Lys Arg Gly Arg Gly Glu Ser Gly Pro Pro Gly Gln Pro Gly
    130                 135                 140

Pro Gln Gly Pro Pro Gly Pro Lys Gly Asp Lys Gly Glu Gln Gly Asp
145                 150                 155                 160

Gln Gly Pro Arg Met Val Phe Pro Lys Ile Asn His Gly Phe Leu Ser
                165                 170                 175

Ala Asp Gln Gln Leu Ile Lys Arg Arg Leu Ile Lys Gly Asp Gln Gly
            180                 185                 190

Gln Ala Gly Pro Pro Gly Pro Pro Gly Pro Pro Gly Pro Arg Gly Pro
        195                 200                 205

Pro Gly Asp Thr Gly Lys Asp Gly Pro Arg Gly Met Pro Gly Val Pro
    210                 215                 220

Gly Glu Pro Gly Lys Pro Gly Glu Gln Gly Leu Met Gly Pro Leu Gly
225                 230                 235                 240

Pro Pro Gly Gln Lys Gly Ser Ile Gly Ala Pro Gly Thr Pro Gly Met
                245                 250                 255

Asp Gly Gln Lys Gly Glu Pro Gly Ser Pro Gly Ala Ala Gly Gln Ser
            260                 265                 270

Gly Leu Pro Gly Pro Lys Gly Glu Pro Gly Lys Glu Gly Glu Lys Gly
        275                 280                 285

Asp Ala Gly Glu Asn Gly Pro Lys Gly Asp Thr Gly Glu Lys Gly Asp
290                 295                 300

Pro Gly Ser Ser Ala Ala Gly Ile Lys Gly Glu Pro Gly Glu Ser Gly
305                 310                 315                 320

Arg Pro Gly Gln Lys Gly Glu Pro Gly Leu Pro Gly Leu Pro Gly Leu
                325                 330                 335

Pro Gly Ile Lys Gly Glu Pro Gly Phe Ile Gly Pro Gln Gly Glu Pro
            340                 345                 350

Gly Leu Pro Gly Leu Pro Gly Thr Lys Gly Asp Arg Gly Glu Ala Gly
        355                 360                 365

Pro Pro Gly Arg Gly Glu Arg Gly Asp Pro Gly Ala Pro Gly Pro Lys
370                 375                 380

Gly Lys Gln Gly Glu Ser Gly Ala Arg Gly Pro Lys Gly Ser Lys Gly
385                 390                 395                 400

Asp Arg Gly Asp Lys Gly Asp Ser Gly Ala Leu Gly Pro Arg Gly Pro
                405                 410                 415

Pro Gly Gln Lys Gly Asp Pro Gly Ala Thr Glu Ile Ile Asp Tyr Asn
            420                 425                 430

Gly Asn Leu His Glu Ala Leu Gln Arg Ile Thr Thr Leu Thr Val Thr
        435                 440                 445
```

Gly Pro Pro Gly Pro Pro Gly Pro Gln Gly Leu Gln Gly Pro Lys Gly
    450                 455                 460

Glu Gln Gly Ser Pro Gly Ile Pro Gly Val Asp Gly Glu Gln Gly Leu
465                 470                 475                 480

Lys Gly Ser Lys Gly Asp Met Gly Asp Pro Gly Val Pro Gly Glu Lys
                485                 490                 495

Gly Gly Leu Gly Leu Pro Gly Leu Pro Gly Ala Asn Gly Val Lys Gly
            500                 505                 510

Glu Lys Gly Asp Thr Gly Leu Pro Gly Pro Gln Gly Pro Ser Ile Ile
        515                 520                 525

Gly Pro Pro Gly Pro Pro Gly Pro His Gly Pro Pro Gly Pro Met Gly
    530                 535                 540

Pro His Gly Leu Pro Gly Pro Lys Gly Ala Ser Gly Leu Asp Gly Lys
545                 550                 555                 560

Pro Gly Ser Arg Gly Ala Asp Gly Pro Ile Gly Pro His Gly Pro Ala
                565                 570                 575

Gly Pro Lys Gly Glu Arg Gly Glu Lys Gly Ala Met Gly Glu Pro Gly
            580                 585                 590

Pro Arg Gly Pro Tyr Gly Leu Pro Gly Lys Asp Gly Glu Pro Gly Leu
        595                 600                 605

Asp Gly Phe Pro Gly Pro Arg Gly Glu Lys Gly Asp Leu Gly Glu Lys
    610                 615                 620

Gly Glu Lys Gly Phe Arg Gly Val Lys Gly Glu Lys Gly Glu Pro Gly
625                 630                 635                 640

Gln Pro Gly Leu Asp Gly Leu Asp Ala Pro Cys Gln Leu Gly Pro Asp
                645                 650                 655

Gly Leu Pro Met Pro Gly Cys Trp Gln Lys
            660                 665

<210> SEQ ID NO 50
<211> LENGTH: 245
<212> TYPE: DNA
<213> ORGANISM: Mus musculus

<400> SEQUENCE: 50
acagagaatt accaccttaa ctgtcacggg ccccccctgga cctcctggac ctcaaggact     60
acaagggcca aagggtgagc aaggctctcc aggaatcccc ggagttgatg agaacaggg     120 actcaaaggc tccaagggag acatggggga cccaggtgtg ccaggtgaaa aggaggact     180 gggacttcct ggattgccgg gtgccaatgg agtaaaagga gagaaggag acaccggttt     240 gccag                                                                 245

<210> SEQ ID NO 51
<211> LENGTH: 73
<212> TYPE: DNA
<213> ORGANISM: Mus musculus

<400> SEQUENCE: 51
agaaatccta cgaatatatg gctaaaataa gaacggtcag ggaggcacct ttagagtgca     60
actgcccagc agg                                                        73

<210> SEQ ID NO 52
<211> LENGTH: 502
<212> TYPE: DNA
<213> ORGANISM: Mus musculus

<400> SEQUENCE: 52

```
actgcccagc aggtcctcca gggaaacgag ggaagagagg ccgaagagga gaatctggtc      60
ctcctggtca gcctggtcct cagggccctc ctggtccaaa aggtgataag ggagaacaag     120
gtgatcaggg acctcggatg gtgtttccta aaatcaatca cggctttctc tctgctgatc     180
agcagctcat taaacgccgg ctgattaagg gtgaccaagg acaggcaggg cctccaggac     240
ctccaggccc tcctggtcca agaggccac ctggggacac aggaaaggac ggccccgag      300 gaatgccagg agtacctggt gaaccaggaa accaggaga acaaggcttg atgggacctc     360
tggggcctcc aggacaaaag ggttccattg gagcacctgg accccaggc atggatgggc     420 aaaagggtga gcctggatca cctggagcag ccgggcagag tggactacca ggacctaagg     480
gagaacctgg aaaagaagga ga                                              502

<210> SEQ ID NO 53
<211> LENGTH: 495
<212> TYPE: DNA
<213> ORGANISM: Mus musculus

<400> SEQUENCE: 53
aaaagggtga ccctggatca tctgctgcag gaattaaggg agaacctgga gaatctggcc      60
gcccggggca aagggtgaa ccagggctgc ctgggctgcc tggacttccg ggaataaagg     120
gagaaccagg cttcattggt cctcaaggag aaccagggtt accagggcta ccaggaacaa     180
aaggtgatcg tggggaggcg gggcctcctg gaagaggtga acgaggagat cctggagccc     240
cggggccaaa ggggaagcaa ggtgaatcag gagctagagg cccgaagggg tcaaagggtg     300
atcgtggaga caaaggagac tctggcgctc tgggaccacg gggtccacct ggacaaaagg     360
gggatccagg agccacagag atcatagact acaatggcaa cctccatgag gccttacaga     420
gaattaccac cttaactgtc acgggccccc ctggacctcc tggacctcaa ggactacaag     480
ggccaaaggg tgagc                                                      495

<210> SEQ ID NO 54
<211> LENGTH: 572
<212> TYPE: DNA
<213> ORGANISM: Mus musculus

<400> SEQUENCE: 54
cccggcgcca cacagtcccc ggccggaggg tgcttttcac tcctagctgg aaggggagaa      60
agaatctgga ggacggtcgg tccacgcctg ctgatccgga cgccgagcca cgcgcaggtc     120
catctctaag cccgggctcc gactctacca actagttgtg cagccgcagg gactgaactt     180
tggaggaacc gacccttcct ctcattctaa gattactgga ggagatagaa ggtgggaaggc     240 gtagcggagg ccagcgaccc cgccacaatg ttggtgaaga agcttgcagg gaaaggaggg     300
ggacgagagt ctggatcaga agatccgcgc cccttgggac agcgttgtgc cggcaccatg     360
ccctcgtgca cggccctggc gaccctcttg tcagtggttg ctgtggcttt ctgtttttat     420
cttggggtga aaaccaacga cctccaggcg aggattgttg ctcttgaatc tgctaaaggg     480
accccttcct tccatccgct gtctgacacc gtggatgagc tgaaggcaat ggttcaggag     540
aaagtggagc gtctcttggc tcagaaatcc ta                                   572

<210> SEQ ID NO 55
<211> LENGTH: 427
<212> TYPE: DNA
<213> ORGANISM: Mus musculus

<400> SEQUENCE: 55
```

```
gtcctcaggg gccttctatc ataggcccac caggccctcc aggtccccat ggcccacctg      60
gtcccatggg gccccatgga cttcctggac caaagggagc atctggctta gacggaaagc     120
caggatcccg gggtgcagat ggtcctatag gaccccacgg ccctgcagga cccaaaggag     180
aaagaggaga gaaaggagct atgggagagc ctggacccag agggccctat gggctgcctg     240
gcaaagatgg agaacctggt cttgatggct tccctggtcc tcgaggcgag aagggtgacc     300
tgggagaaaa gggagaaaag ggattccgtg gcgttaaggg ggaaaagggg gagccaggcc     360
agcctggcct ggatgggctg gatgctcctt gccaattggg acctgatggg ttacctatgc     420
ctggctg                                                              427

<210> SEQ ID NO 56
<211> LENGTH: 47
<212> TYPE: DNA
<213> ORGANISM: Mus musculus

<400> SEQUENCE: 56
gctgctggca aaagtgatga atctaacctt ccgagcatga agttgtg                   47
```

COLLAGEN-LIKE PROTEIN CLAC, A PRECURSOR THEREOF, AND GENES ENCODING THE SAME

This application is a continuation application of U.S. application Ser. No. 12/329,171 filed Dec. 5, 2008 now U.S. Pat. No. 7,888,076, which is a divisional application of U.S. application Ser. No. 10/203,561, filed Aug. 12, 2002, now U.S. Pat. No. 7,514,542.

The present invention relates to a human-type collagen-like protein (CLAC) and a precursor thereof (CLAC-P) in amyloid that accumulates in Alzheimer's brain and forms senile plaques; and genes encoding them. Further the present invention relates to a cDNA and an amino acid sequences of mouse-type CLAC-P. The present invention also relates to development of: a method for treating of Alzheimer's disease by inhibiting a mechanism of accumulation of amyloid proteins, a method for treating Alzheimer's disease by inhibiting cell injury, and a method for diagnosing Alzheimer's disease.

BACKGROUND OF THE INVENTION

Alzheimer's disease is a dementing neurodegenerative disease characterized by formation of senile plaques and neurofibrillary degeneration as well as degeneration of neurons. Senile plaques that are most characteristic of this disease are lesions composed mainly of amyloid-beta peptide (Aβ) derived from beta-amyloid precursor protein (βAPP) (Biochem Biopys Res Commun 122, 1131 (1984)), with apolipoprotein E (Brain Res 541, 163 (1984)) and a complement component C1q (Acta Neuropathol 57, 239 (1982)), etc being deposited. Aβ aggregates by itself, and formation of amyloid fiber is promoted by actions of non-Aβ amyloid components such as apolipoprotein E (Nature 372, 92 (1994)) and C1q (J Neurosci Res 46, 58 (1996)) as above described. Aβ consisting of 40-42 amino acids is secreted from various cells including neurons, and it is not toxic to cells at a normal concentration. However at a higher concentration, Aβ aggregates and becomes toxic to neurons (Science 250, 279 (1990)). In this process, it is known that several molecules such as RAGE (Nature 382, 685 (1996)) and scavenger receptor A (Nature 382, 716 (1996)) are present on the cell surface and act as receptors for aggregated Aβ. It seems that aggregation, accumulation, and toxicity to cells of amyloid are very important in neuronal degeneration process of Alzheimer's disease; therefore, inhibition of these processes will be an effective therapeutic method for Alzheimer's disease.

Accumulation of Aβ as amyloid is very characteristic of Alzheimer's disease, however it is being clarified that only accumulation of Aβ is not sufficient for toxicity to neurons as well as for the development of Alzheimer's disease (J. neurosci. 17, 7053 (1997)). On the other hand, as inferred from the fact that genetic polymorphism of proteins such as apolipoprotein E which promotes accumulation process of senile plaque amyloid serves as a risk factor for development of Alzheimer's disease (Science 261, 921 (1993)). It has been noted that unknown proteinaceous components in amyloid can greatly influence the accumulation and neuronal injury by amyloid; however the responsible components have not been identified yet.

SUMMARY OF THE INVENTION

Taking circumstances above mentioned into consideration, the inventors produced mouse monoclonal antibodies to an amyloid fraction extracted from of a brain of a patient with Alzheimer's disease, and surprisingly found a monoclonal antibody among these antibodies which selectively stains senile plaque amyloid and biochemically recognizes a novel protein of 50 to 100 kilodaltons.

Further the inventors studied the amyloid deposits on the basis of these findings, and found a novel human collagen-like Alzheimer amyloid plaque component (CLAC), and succeeded in obtaining entire structure of CLAC and cloning a novel gene encoding entire CLAC and a precursor thereof (CLAC-P). Further the inventors determined cDNA sequence of mouse-type CLAC-P, and deduced the amino acid sequence.

The present invention relates to:

(1) CLAC DNA comprising a nucleotide sequence of nucleotide 868 to nucleotide 2493 shown in SEQ ID NO: 1, (2) CLAC comprising an amino acid sequence of amino acid 113 to amino acid 654 shown in SEQ ID NO: 2, (3) A DNA encoding a protein in which one or plural amino acids are inserted into, deleted from, or substituted in CLAC defined in (2), said encoded protein having following properties:

(a) accumulating in senile plaque amyloid component of Alzheimer's disease, and (b) having a function of promoting aggregation of Aβ, (4) A DNA which hybridizes to the DNA defined in (1) under a stringent condition, and encodes a protein having the following properties:

(a) accumulating in senile plaque amyloid component of Alzheimer's disease, and (b) having a function of promoting aggregation of Aβ, (5) A protein encoded by a DNA defined in (3) or (4), (6) CLAC-P DNA comprising a nucleotide sequence of nucleotide 532 to nucleotide 2493 shown in SEQ ID NO: 1, (7) CLAC-P comprising an amino acid sequence shown in SEQ ID NO: 2, (8) A DNA encoding a protein in which one or plural amino acids are inserted into, deleted from, or substituted in CLAC-P defined in (7), said encoded protein functioning as an Aβ receptor on cell surface, (9) A DNA which hybridizes to a DNA defined in (6) under a stringent condition and encodes a protein functioning as an Aβ receptor on cell surface,

(10) A protein encoded by a DNA defined in (8) or (9),

(11) A protein defined in (10) in which one or more amino acids are deleted from or substituted in a region of amino acid 141 to 146, or amino acid 589 to 597 shown in SEQ ID NO: 2,

(12) An expression vector containing a DNA defined in any one of (1), (3) and (4),

(13) A transformant transformed by a vector defined in (12),

(14) A method for producing a recombinant protein, which comprises culturing a transformant defined in (13) under a condition enabling an expression vector defined in (12) to be expressed,

(15) An expression vector containing a DNA defined in any one of (6), (8) and (9),

(16) A transformant transformed by a vector defined in (15),

(17) A method for producing a recombinant protein, which comprises culturing a transformant defined in (16) under a condition enabling an expression vector defined in (15) to be expressed,

(18) A transformant deposited to International Patent Organism Depositary, National Institute of Advanced Industrial Science and Technology (AIST Tsukuba Central 6, 1-1, Higashi 1-Chome, Tsukuba-shi, Ibaraki-ken, 305-8566, Japan) under accession No. FERM BP-7438,

(19) CLAC-P gene contained in a transformant defined in (18),

(20) A method for producing a recombinant protein, which comprises culturing a transformant defined in (18) under a condition enabling a vector contained therein that contains CLAC-P gene to be expressed,

(21) An antibody which specifically binds to a protein defined in (2) or (5),

(22) An antibody defined in (21) which is a monoclonal antibody 9D2,

(23) A method for screening an inhibitor of CLAC activity, which comprises using a protein defined in (2) or (5).

(24) An inhibitor of CLAC activity obtainable by a screening method defined in (23),

(25) A method for detecting CLAC, which comprises using an antibody defined in (21),

(26) A method for treating of, delaying progress of, or preventing Alzheimer's disease, which comprises using an antibody defined in (21) or an inhibitor of CLAC activity defined in (24),

(27) A method defined in (25), in which the antibody is monoclonal antibody 9D2,

(28) A method defined in (26), in which the antibody is monoclonal antibody 9D2,

(29) A method for purifying CLAC, which comprises using monoclonal antibody 9D2,

(30) An antibody which specifically binds to a protein defined in any one of (7), (10) and (11),

(31) An antibody defined in (30), which is monoclonal antibody 9D2,

(32) A method for screening an inhibitor of CLAC-P activity, which comprises using a protein defined in one of (7), (10) and (11),

(33) An inhibitor of CLAC-P activity obtainable by a screening method defined in (32),

(34) A method for detection of CLAC-P, which comprises using an antibody defined in (30),

(35) A method for treating of, delaying progress of, or preventing Alzheimer's disease, which comprises using an antibody defined in (30) or an inhibitor of CLAC-P activity defined in (33),

(36) A method defined in (34), in which the antibody is monoclonal antibody 9D2,

(37) A method defined in (35), in which the antibody is monoclonal antibody 9D2,

(38) A method for purifying CLAC-P, which comprises using monoclonal antibody 9D2,

(39) A kit for diagnosing Alzheimer's disease, which comprises detectably labeled monoclonal antibody 9D2,

(40) A transgenic animal in which a DNA defined in any one of (1), (3), (4), (6), (8) and (9) is artificially inserted into, or deleted from the chromosome.

BRIEF DESCRIPTION OF THE DRAWINGS

FIGS. 1A and 1B show CLAC-P cDNA nucleotide sequence (SEQ ID NO:1) and deduced amino acid sequence corresponding thereto (SEQ ID NO: 2), respectively.

FIG. 3 shows cDNA nucleotide sequence of mouse CLAC-P (SEQ ID NO: 48).

FIG. 4 shows deduced amino acid sequence of mouse CLAC-P (SEQ ID NO: 49).

DETAILED DESCRIPTION OF THE PREFERRED EMBODIMENTS

Figure 2:
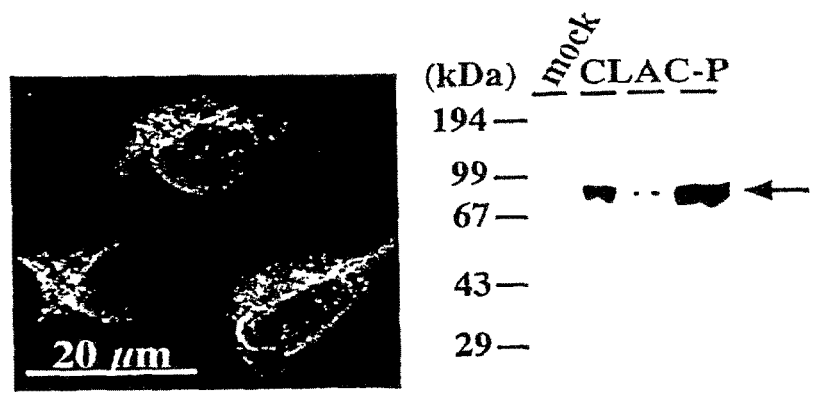
FIG. 2 shows 9D2 immunostaining of HEK293 cells expressing CLAC-P (left panel, A) and Western blot of a HEK293 cell membrane fraction expressing CLAC-P (right panel, B).

The first aspect of the present invention is a DNA comprising a nucleotide sequence of nucleotide 868 to nucleotide 2493 shown in SEQ ID NO: 1, which encodes CLAC.

The second aspect of the present invention is CLAC having an amino acid sequence of amino acid 113 to amino acid 654 shown in SEQ ID NO: 2.

Novel amyloid molecules CLAC and CLAC-P of the present invention can be detected by use of specific interaction with antibodies, as described in Example 2. Partial amino acid sequences, cDNA sequence, and amino acid sequence thereof can also be determined. These procedures are briefly described below.

CLAC and CLAC-P can be detected, for example by following methods:

A mouse, for example BALB-C mouse is immunized with senile plaque amyloid components which are partially purified as an insoluble fraction from brain of a patient with Alzheimer's disease by known methods such as sucrose density gradient centrifugation and urea extraction, and then antibodies, preferably a monoclonal antibody is obtained. Using the antibody thus obtained, CLAC and CLAC-P can be detected according to a method (i) or (ii) described below:

(i) After cerebral cortex obtained from a patient with Alzheimer's disease is fixed in 10% formalin, tissue sections are immunochemically stained, and CLAC or CLAC-P is detected as an amyloid plaque, or (ii) After cerebral cortex obtained from a patient with Alzheimer's disease is extracted with Tris-buffer and sodium dodecyl sulfate, the precipitation thus formed is dissolved in 70% formic acid to obtain an amyloid fraction. The amyloid fraction is subjected to SDS-electrophoresis and Western blot analysis, and CLAC or CLAC-P is detected as a polypeptide of 50 to 100 kilodaltons.

Preferable antibody used is monoclonal antibody 9D2 described in Example 1.

Partial amino acid sequences of CLAC of the present invention can be determined, for example by following steps (i) to (v):

(i) After cerebral cortex obtained from a patient with Alzheimer's disease is extracted with Tris-buffer and sodium dodecyl sulfate (SDS), the precipitation thus formed is dissolved in 70% formic acid. Amyloid component thus obtained is submitted to reverse phase high performance liquid chromatography (HPLC), and fractionated to be separated from Aβ peptide, (ii) 50 kDa and 100 kDa polypeptides are isolated respectively by gel filtration column, (iii) The polypeptide is partially hydrolyzed by a protease such as lysylendopeptidase, Asp-N or trypsin, (iv) Peptide fractions are separated by reverse phase HPLC, and (v) The amino acid sequence of the peptide is determined by an amino acid sequence analyzer.

cDNA nucleotide sequence of a precursor of CLAC, i.e. CLAC-P can be obtained by, for example a method comprising following steps (i) and (ii):

(i) Using synthetic oligonucleotide mixture (degenerate primers) as primers which correspond to nucleotide sequence encoding a part of a partial amino acid sequence of CLAC obtained as mentioned above, for example a part of Gly Glu Gln Gly Asp Gln Gly Pro Arg Met Val Phe Pro Lys Ile Asn His Gly Phe Leu Ser Ala Asp Gln Gln Leu Ile Lys (SEQ ID NO: 11), cDNA encoding a part of CLAC protein is cloned from a complementary DNA (cDNA) library of human brain by use of polymerase chain reaction (PCR), and (ii) Using the nucleotide sequence obtained in step (i) as a template, "rapid amplification of cDNA ends" method known in the art is repeated.

Also, deduced entire amino acid sequence can be obtained by translating the nucleotide sequence above mentioned into an amino acid sequence according to a standard method.

The cDNA sequence of human CLAC-P thus obtained is shown in SEQ ID NO: 1. This sequence has an ORF (open reading frame) (nucleotides 532 to 2493) encoding CLAC-P consisting of 654 amino acids, and the deduced entire amino acid sequence of CLAC-P of the 654 amino acids is shown in SEQ ID NO: 2.

Alternatively, using cDNA library derived from mouse or rat brain, and by synthesizing oligonucleotides corresponding to the nucleotide sequence appropriately selected from human CLAC-P nucleotide sequence, and using them as primers, PCR method can be performed to obtain mouse or rat CLAC-P cDNA and amino acid sequences thereof.

CLAC of the present invention has following functions: (a) it accumulates in senile plaque amyloid of Alzheimer's disease, (b) it promotes aggregation of Aβ.

Function of CLAC of the present invention to promote Aβ aggregation can be estimated by various methods, for example following methods (1) or (ii):

(i) One hundred and fifteen μM of synthetic Aβ (1-42) peptide [which means that the peptide consists of amino acids 1 to 42 from the N-terminal] and an appropriate amount of purified CLAC are mixed, and incubated for 0 to 5 days at room temperature. The reaction mixture is centrifuged at 15,000×g for 15 min, and the precipitation is suspended in 10 μl of PBS solution. An appropriate amount of thioflavin T is added, and analysis is performed in a fluorescence photometer. λex is 440 mn, and λem is 482 nm. Fluorescence obtained is compared with that obtained by incubation with Aβ (1-42) only (without purified CLAC), alternatively (ii) it is immunochemically or biochemically identified that more beta-amyloid plaques are found in brain of a mouse generated by mating a transgenic mouse over-expressing human CLAC-P gene with a mouse over-expressing Alzheimer mutant βAPP gene, than in brain of a transgenic mouse expressing excess Alzheimer mutant βAPP gene only; or it is immunochemically or biochemically identified that less beta-amyloid plaques are found in a CLAC-P gene knock-out mouse over-expressing Alzheimer mutant βAPP gene, than in a transgenic mouse over-expressing Alzheimer mutant βAPP gene.

The third aspect of the present invention is a DNA encoding variant CLAC protein, in which one or plural amino acids are inserted into, deleted from, or substituted in CLAC amino acid sequence, said variant CLAC protein (a) accumulates in senile amyloid component of Alzheimer's disease, and (b) promotes Aβ aggregation.

Here, insertion, deletion or substitution of one or plural amino acids can be occurred artificially or naturally. For example, by known methods in gene-engineering such as site-specific mutagenesis (M. J. Zoller et al., Methods in Enzymology, 100, 468 (1983)) or PCR method (Molecular Cloning 2nd Ed. Ch. 15, Cold Spring Harbor Laboratory Press (1989)), these mutations can be occurred. In addition such insertion, deletion or substitution of one or plural amino acids can be occurred in vivo. Variants such as splice variants and allelic variants are included in variant CLAC protein of the present invention. Moreover partial peptides of CLAC which have the functions (a) and (b) above mentioned are included in variant CLAC protein of the present invention. Proteins in which one or plural amino acids are chemically modified (artificial or naturally occurring) are also included in variant CLAC protein of the present invention. Such modifications include, for example acetylation, amidation, acylation, addition of sugar chain, phosphorylation, sulfation, addition of lipid, halogenation, formation of salt, etc. Moreover amino acids other than naturally occurring twenty L-amino acids (such as D-amino acids, artificial amino acids) can exist in variant CLAC protein. Homology of a DNA sequence encoding such a variant CLAC protein to a DNA sequence encoding the original CLAC (the first aspect of the present invention) is at least 50%, preferably at least 70%, more preferably at least 80%, most preferably at least 90%.

Here, homology means a degree of match between two nucleotide sequences or amino acid sequences, which is expressed by percentage. Currently computer software-programs such as Smith-Waterman algorithm, FASTA or BLAST program, etc. are used to determine homology.

The fourth aspect of the present invention is a DNA which hybridizes to the DNA defined in SEQ ID NO: 3 under a stringent condition, and encodes a protein having the following properties: (a) accumulating in senile plaque amyloid component of Alzheimer's disease, and (b) having a function of promoting aggregation of Aβ. Here, "stringent condition" means a condition, for example in which hybridization occurs only when the nucleotide sequences have more than 90% homology. As example of stringent condition is: incubation at 42° C. overnight in a solution containing 50% formamide, 5×SSC (150 mM NaCl, 15 mM sodium citrate), 50 mM sodium phosphate (pH 7.6), 5× Denhart's solution, 10% dextran sulfate, and 20 ug/ml of denatured and sheered salmon sperm DNA, then washing in 0.1×SSC at 65° C. Hybridization and washing can be performed by known methods described in for example, Molecular Cloning 2nd Ed. Ch. 11, Cold Spring Harbor Laboratory Press (1989) etc.

The fifth aspect of the present invention is a protein encoded by either DNA:

(i) a DNA encoding a variant CLAC protein in which one or plural amino acids are inserted into, deleted from, or substituted in CLAC protein shown in SEQ ID NO: 4, said variant CLAC protein (a) accumulates in senile plaque component of Alzheimer's disease, and (b) promotes Aβ aggregation; or (ii) a DNA hybridizing to the DNA shown in SEQ ID NO: 3 under a stringent condition, said DNA encodes a protein which (a) accumulates in senile plaque component of Alzheimer's disease, and (b) promotes Aβ aggregation.

Such proteins include variant CLAC proteins and proteins having high amino acid sequence homologies to CLAC, which have the functions (a) and (b) above mentioned. Embodiments of such proteins include for example variant CLAC proteins above described, partial peptides of CLAC, and rat or mouse CLAC, etc.

In this specification, CLAC of the second aspect and variant CLAC of the fifth aspect can be collectively referred to "CLAC".

The sixth aspect of the present invention is CLAC-P DNA comprises a nucleotide sequence of nucleotide 532 to nucleotide 2493 shown in SEQ ID NO: 1.

The seventh aspect of the present invention is CLAC-P comprises an amino acid sequence shown in SEQ ID NO: 2.

CLAC-P of the present invention functions as an Aβ receptor on cell surface.

Function of CLAC-P of the present invention as an beta-amyloid receptor can be estimated by various methods, for example following method:

HEK293 cells permanently expressing CLAC-P and control cells are cultivated to confluent state, and 10 μM Aβ (1-42) preincubated in a tube for 60 min is added, and incubated for 60 min. Cells collected are solubilized with SDS sample buffer by sonication, and separated by SDS-polyacrylamide gel electrophoresis, and Western blotting is performed using anti-Aβ antibody, then an amount of Aβ bound to cells can be determined.

Cytotoxicity of Aβ bound to cells via CLAC-P can be estimated by following method: for example, PC 12 cells having been induced to differentiate to nerve cells are made to transiently express CLAC-P by lipofection method, and Aβ (1-42) preincubated for 1 hr is added, and incubated for 1 hr. Thereafter cells are fixed by 10% formalin, and nuclei showing apoptosis are stained by TUNEL staining, and then ratio of positive cells is compared with that of PC12 cells which do not express CLAC-P. Alternatively, 3-[4,5-dimethylthiazole-2-yl]-2,5-diphenoltetrazolium bromide (MTT) reagent is added to each well, and amount of MTT reagent incorporated into living cells may be measured by a spectrophotometer and compared.

The eighth aspect of the present invention is a DNA encoding variant CLAC-P protein in which one or plural amino acids of CLAC-P are inserted, deleted or substituted, said variant CLAC-P protein functions as an Aβ receptor on cell surface.

Here, insertion, deletion or substitution of one or plural amino acids can be occurred artificially or naturally. For example, by known methods in gene-engineering such as site-specific mutagenesis (M. J. Zoller et al., Methods in Enzymology, 100, 468 (1983)) or PCR method (Molecular Cloning 2nd Ed. Ch. 15, Cold Spring Harbor Laboratory Press (1989)), these mutations can be occurred. In addition such insertion, deletion or substitution of one or plural amino acids can be occurred in vivo. Variants such as splice variants and allelic variants are included in variant CLAC-P protein of the present invention. Moreover partial peptides of CLAC-P which functions as an Aβ receptor on cell surface are included in variant CLAC-P protein of the present invention. Proteins in which one or plural amino acids are chemically modified (artificial or naturally occurring) are also included in variant CLAC-P protein of the present invention. Such modifications include, for example acetylation, amidation, acylation, addition of sugar chain, phosphorylation, sulfation, addition of lipid, halogenation, formation of salt, etc. Moreover amino acids other than naturally occurring twenty L-amino acids (such as D-amino acids, artificial amino acids) can exist in variant CLAC-P protein. Homology of a DNA sequence encoding such a variant CLAC-P protein to a DNA sequence encoding the original CLAC-P (the sixth aspect of the present invention) is at least 50%, preferably at least 70%, more preferably at least 80%, most preferably at least 90%.

The ninth aspect of the present invention is a DNA hybridizing to a DNA shown in SEQ ID NO: 1 in a stringent condition, which encodes a protein that functions an Aβ receptor on cell surface.

The tenth aspect of the present invention is a protein encoded by either DNA:

(i) a DNA encoding a variant CLAC-P protein in which one or plural amino acids of CLAC-P are inserted, deleted or substituted, said variant CLAC-P protein functions as an Aβ receptor on cell surface; or (ii) a DNA hybridizing to the DNA shown in SEQ ID NO: 1 under a stringent condition, said DNA encodes a protein which functions as an Aβ receptor on cell surface.

Such proteins include variant CLAC-P proteins and proteins having high amino acid sequence homologies to CLAC-P, which functions as an Aβ receptor on cell surface. Embodiments of such proteins include for example variant CLAC-P proteins above described, partial peptides of CLAC-P, and rat or mouse CLAC-P, etc.

Further, the eleventh aspect of the present invention is a splice variant of CLAC-P of the present invention. Examples of splice variants of CLAC-P of the present invention are a polypeptide shown in SEQ ID NO: 2, in which one to six amino acids locating amino acid positions 141-146 are deleted or substituted; or a polypeptide shown in SEQ ID NO: 2, in which one to nine amino acids locating amino acid positions 589-597 are deleted or substituted; or a polypeptide shown in SEQ ID NO: 2, in which both deletion or substitution above described exist at the same time. Such a variety seems to be attributed to formation of plural kinds of messenger RNA by alternative selective splicing.

In this specification, CLAC-P of the seventh aspect, variant CLAC-P protein of tenth aspect, and splice variant of CLAC-P of eleventh aspect can be collectively referred to "CLAC-P".

The twelfth aspect of the present invention is an expression vector containing a DNA any one of the first, the third, or the fourth aspect of the present invention. The thirteenth aspect of the present invention is a transformant which is transformed by said expression vector. The fourteenth aspect of the present invention is a method for producing a recombinant protein, which comprises culturing said transformant under a condition enabling said vector to be expressed. The recombinant protein thus produced is also included in the present invention. Such a recombinant protein is CLAC of any one of the present invention, or variant CLAC protein which (a) accumulates in senile plaque amyloid component of Alzheimer's disease, and (b) promotes Aβ aggregation.

The fifteenth aspect of the present invention is an expression vector containing a DNA of any one of the sixth, the eighth, or the ninth aspect of the present invention. The sixteenth aspect of the present invention is a transformant transformed by said expression vector. The seventeenth aspect of the present invention is a method for producing a recombinant protein, which comprises culturing said transformant under a condition enabling said vector to be expressed. The recombinant protein thus produced is also included in the present invention. Such a recombinant protein is CLAC-P of the present invention, or variant CLAC-P protein which functions as an Aβ receptor on cell surface. In aspects relating these aspects, the present invention relates to a HEK293 cell transformant (deposited to International Patent Organism Depository, National Institute of Advanced Industrial Science and Technology (AIST Tsukuba Central 6, 1-1, Higashi 1-Chome, Tsukuba-shi, Ibaraki-ken, 305-8566, Japan) under accession No. FERM BP-7438) in which a vector is inserted that contains a gene encoding CLAC-P. Thus, the present invention also relates to the CLAC-P gene contained in the deposited strain above mentioned. In further aspect, the present invention relates to a method for producing a recombinant protein, which comprises culturing the transformed strain deposited under a condition enabling the vector therein containing CLAC-P gene to be expressed. The recombinant protein thus produced is also included in the present invention.

Recombinant proteins can be produced by known methods in the art, for example the method described in Molecular Cloning 2nd Ed., Cold Spring Harbor Laboratory Press (1989). Representative methods are described:

Vectors suitable for integration of DNA above described include, but are not limited to pBR322 (Gene, 2, 95 (1977)), pBR325 (Gene, 4, 121 (1978)), pUC12 (Gene, 19, 259 (1982)), pUC13 (Gene, 19, 259 (1982)), pUC118, pUC119 (Methods in Enzymology, 153, 3 (1987)) from *Escherichia coli*, pUB110 (Biochemical and Biophysical Research Communication, 112, 678 (1983)) from *Bacillus*. Other vectors can be used which can replicate and are maintained in the host.

A method for integration of the DNA above mentioned includes, for example the method described in Molecular Cloning p. 239, Cold Spring Harbor Laboratory Press (1982).

A plasmid thus obtained is introduced into a suitable host such as *Escherichia* and *Bacillus* strains.

Examples of *Escherichia* strains are, but not limited to *Escherichia coli* K12DH1 (Proc. Natl. Acad. Sci. USA, 60, 160 (1986)), M103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)).

A method for transformation includes, for example calcium chloride method described, or calcium chloride/rubidium chloride method described in Molecular Cloning p. 249, Cold Spring Harbor Laboratory Press (1982).

Desired clones are selected from transformants thus obtained, by known methods in the art such as colony hybridization method (Gene, 10, 63 (1980)) and DNA sequencing method (Proc. Natl. Acad. Sci. USA, 78, 560 (1977); Nucleic Acids Research, 9, 309 (1981)).

As described above, microorganism are obtained which retain a vector carrying a DNA containing cloned gene of the protein of the present invention.

Then, the plasmid is isolated from the microorganism.

A method for isolation includes, but not limited to alkali method (H. C. Birmbiom et al., Nucleic Acids Research, 1, 1513 (1979)).

A plasmid having DNA containing cloned gene of the protein of the present invention, can be used without treatment, or used after cleavage by restriction enzyme(s).

An expression vector can be obtained by ligating the cloned gene of the protein of the present invention into downstream of a promoter of a vehicle (vector) suitable for expression. Preferred hosts being transformed by the expression vector are animal cells, and preferred vectors include expression plasmids for animal cells (for example pcDNA I, pdKCR-dhfr, etc). Vectors suitable, for example, for bacterial cells, fungal cells, insect cells, plant cells can be used so long as they are suitable for production of the recombinant proteins of the present invention, and such vectors are well known in the art.

Said gene may have ATG as a start codon (and optionally a nucleotide sequence encoding a suitable signal peptide) at the 5' terminal, or may have TAA, TGA or ATAG (preferably TGA) as a termination codon at the 3' terminal. Further, promoter(s) is(are) connected to the upstream of the gene for expression.

Any expression promoters compatible with the host can be used in the present invention.

When the host is an animal cell, promoters derived from SV40, promoters of retroviruses (not limited to these) can be used, preferably SV40 promoter is used.

Animal cells include, but not limited to monkey COS-7 cell, Chinese hamster ovary cells (CHO cells), neuroblastoma cells, glia cells, fibroblasts. Preferred cells are those that express and secrete much protein of the present invention, and particularly preferable cell is human embryonic kidney fibroblast 293 cell.

To transform animal cells, for example, the method described in Virology, 52, 456 (1973) is performed.

Thus, a transformant is obtained which has been transformed by a vector containing DNA encoding the protein of the present invention.

When a transformant, the host of which is *Escherichia* or *Bacillus* strain, is used, a liquid medium is suitable, in which carbon sources, nitrogen sources, minerals and so on necessary for growth of the transformant are included. Examples of carbon sources are, but not limited to, glucose, dextrin, soluble starch, and sucrose; examples of nitrogen sources are, but not limited to, inorganic or organic materials such as ammonium salts, nitrates, corn steep liquor, corn starch, peptone, casein, meat extract, soybean meal, and potato extract; examples of minerals are, but not limited to, calcium chloride, disodium hydrogenphosphate, and magnesium chloride. Yeast extract, vitamins, growth-promoting factors, etc may also be added to the medium. Preferably pH of the medium is about 6 to about 8.

Preferable medium for cultivation of *Escherichia* strains is, for example M9 medium containing glucose and casamino acid (Journal of Experiments in Molecular Genetics, 431-433, Cold Spring Harbor Laboratory, New York (1972)). If necessary, an reagent such as 3beta-indoacrylic acid can be added to the medium to make promoter effective.

When a host is *Escherichia* strain, usually cultivation is carried out at about 15 to about 43° C., for about 3 to about 24 hours. If necessary, aeration and/or stirring can be added.

When a host is *Bacillus* strain, usually cultivation is carried out at about 30 to about 40° C., for about 6 to about 24 hours. If necessary, aeration and/or stirring can be added.

When a transformant is cultured, the host of which is an animal cell, examples of media are, but not limited to, MEM medium (Science, 122, 501 (1952)), DMEM medium (virology, 8, 396 (1959)), RPMI 1640 medium (The Journal of American Medical Association, 199, 519 (1967)), and 199 medium (Proceeding of the Society for the Biological Medicine, 73 1 (1950)). Five to 20% calf fetal serum can be added to these media. Preferable pH of the media is about 6 to about 8. Usually cultivation is performed at about 30 to about 40° C., and aeration and/or stirring is added, if necessary.

Induced expression vector above described in which the gene of CALC-P or CLAC of the present invention is integrated, can be used not only for a large scale production of the vector (by introducing the vector into a bacterium such as *Escherichia coli*), or production of the recombinant protein of the present invention in various cells, but also for production of transgenic animals as described below.

As above described, CLAC-P is a precursor of CLAC (CLAC is the fragment type thereof), and has an amino acid sequence shown in SEQ ID NO: 2.

Processing of CLAC-P to the fragment type CLAC is performed by cleavage between amino acid 112 (Arg) and amino acid 113 (Glu) of SEQ ID NO: 2. Therefore, amino acid 113 (Glu) to amino acid 654 (Lys) is the amino acid sequence of CLAC. Usually, the first amino acid Glu of CLAC is cyclized to be pyroglutamic acid residue.

CLAC-P is converted to CLAC by actions of processing enzymes in the body. Such processing enzymes are included in the present invention. Such processing enzymes can be identified, for example by any one of the following methods:

(i) For CLAC secreted or produced by cultured cells expressing CLAC-P, the culture broth or extracellular matrix produced around the cells is obtained, and subjected to amino acid analysis, then the cleaved site is determined by comparing with CLAC-P, or (ii) Known protease inhibitor is added to cells expressing CLAC-P, and the amount of CLAC protein produced in the culture broth or in the extracellular matrix is analyzed, using the decrease in the amount of CLAC protein as an indicator, or (iii) Mutation is introduced in the nucleotide sequence of CLAC-P gene to alter amino acid(s) necessary for cleavage by known protease, and the mutated gene is expressed. Then the amount of CLAC protein produced in culture broth or in the extracellular matrix is analyzed, using the decrease of CLAC protein as an indicator, or (iv) cDNA encoding known protease is further introduced into cultured cells expressing CLAC-P, and the amount of CLAC protein produced in the culture broth or the extracellular matrix is analyzed, using the increase of CLAC protein as an indicator, or (v) cDNA encoding CLAC-P is expressed in cultured cells lacking known protease, and cultured. Then the amount of CLAC protein produced in culture broth or in the extracellular matrix is analyzed, using the decrease of CLAC protein as an indicator.

Processing enzymes identified by the methods above mentioned include, but not limited to furin convertase enzyme.

Inhibitors of the proteases include, but not limited to decanoyl-RVKR-chloromethylketone which is a competitive inhibitor of furin convertase and analogous compounds thereof. Cultured cells expressing CLAC-P is useful in an effective and sensitive screening of substances that inhibit production or secretion of CLAC because the cultured cells expressing CLAC-P produce and secrete much CLAC. Screening of such substances can be performed, for example by culturing the transformed cells of the present invention in a medium containing a test substance, and detecting or quantifying the inhibition of CLAC production or secretion. In said screening method, changes in CLAC production or secretion from the cells by the test substance can be detected and quantified, by appropriate methods such as Western blotting method using an antibody specific to CLAC.

Specifically, for example, the transformed cells of the present invention are plated into multi-well plates, and the cells are cultured in a DMEM medium containing serum to be confluent. After the cultured cells are washed in a serum-free medium (DMEM containing 0.5% bovine serum albumin), a test substance is added to the same medium, and cells are cultured for a certain period (for example 24 hours). The amount of CLAC contained in the culture supernatant or in the extracellular matrix attached on the multi-well plate is quantified by Western blotting method. Inhibitory effect of the test substance on CLAC production and/or secretion is estimated by the amount of CLAC compared with that of the group without the test substance, or by the concentration of the test substance to induce decrease of CLAC production and/or secretion.

Because the transformed cells of the present invention can be subcultured, and can produce or secrete much CLAC-P and/or CLAC, they can be used in screening with high efficacy and high reproducibility. Therefore the transformed cells can be advantageously used to screen substances that inhibit CLAC production or secretion. Moreover a great amount of stable cloned cells can be always obtained, which makes screening more stable and effective. Substances identified by such screenings that inhibit CLAC production and secretion are included in the present invention.

A large amount of CLAC can be expressed in cultured cells and purified, for example by, but not limited to following methods (i), (ii), or (iii):

(i) HEK293 cells (ATCC CRL-1573) stably expressing CLAC-P are cultured in DMEM medium containing 10% FBS for 3 days, then when the cells reach to semi-confluency, the cells are cultured in DMEM not containing FBS for 48 hours, then the culture liquid is recovered. The culture liquid is dialyzed against 50 mM Tris-HCl (pH 8.6) at 4° C. overnight, thereafter centrifuged at 250,000×g for 30 minutes. The precipitate is dissolved in 0.1 M acetic acid, and applied to a DEAE column. Stepwise elution is performed with 0 M to 1 M NaCl (0.1 M increment). All fractions are dialyzed against 0.1 M acetic acid, and identification is performed for example by immunoblotting using a specific antibody 9D2, then positive fraction is used as purified CLAC fraction (for general procedures, see Fichard et al., J. Biol. Chem., 272, 30083 (1997)).

(ii) HEK293 cells stably expressing CLAC-P are cultured in DMEM medium containing 10% FBS for 3 days, and when the cells reach to semi-confluency, the cells are cultured in DMEM not containing FBS for 48 hours, then the culture liquid is recovered. The culture liquid is dialyzed against 50 mM Tris-HCl (pH 8.6) at 4° C. overnight, thereafter centrifuged at 250,000×g for 30 minutes. The precipitate is dissolved in 0.15 M acetic acid, and further dialyzed against 20 mM $Na_2HPO_4$—$NaH_2PO_4$ (pH7.2) containing 2 M urea (PB/U solution) overnight, thereafter centrifuged at 250,000×g for 30 minutes, and applied to a heparin column. Stepwise elution is performed with 0 M to 1 M NaCl (0.1 M increment). All fractions are dialyzed against PB/U, and identification is performed for example by immunoblotting using a specific antibody 9D2, then positive fraction is used as purified CLAC fraction (for general procedures, see Mizuno et al., J. Biol. Chem., 120, 934 (1996)).

Or, (iii) CLAC specific antibody (for example 9D2) (1 mg/ml) is previously bound to NHS activated carrier such as Affigel 10 (Bio-Rad) to obtain an antibody column. HEK293 cells permanently expressing CLAC-P are cultured in DMEM medium containing 10% FBS for 3 days, and when the cells reach to semi-confluency, the cells are cultured in DMEM not containing FBS for 48 hours, then the culture liquid is recovered. Proteins in the medium are precipitated with 50% saturated ammonium sulfate. The precipitated proteins are dissolved in IP buffer (TSI solution [50 mM Tris (Gibco BRL), 150 mM NaCl (Kanto Kagaku), 0.5 mM DIFP (Wako Junyaku), 0.5 mM PMSF (Boehringer Mannheim), 1 mM EGTA (Wako Junyaku), 1 μg/ml antipain (Sigma), 1 μg/ml leupeptin (Wako Junyaku), 1 μg/ml pepstatin (Sigma), 1 μg/ml TLCK (Sigma)] containing 0.5% SDS and 0.5% NP-40), filtered by 0.45 μm filter, and applied to the antibody column above described. Elution is performed with 0.2 M glycine-HCl (pH 2.6) containing 0.1% Triton X-100. Eluted fraction is used as purified CLAC (for general procedures, see Hirako et al., J. Biol. Chem., 273, 9711 (1998)).

Therefore, further aspect of the present invention is a method for purification of CLAC using monoclonal antibody 9D2.

Hybridoma producing monoclonal antibody 9D2 has been deposited to International Patent Organism Depositary, National Institute of Advanced Industrial Science and Technology (AIST Tsukuba Central 6, 1-1, Higashi 1-Chome, Tsukuba-shi, Ibaraki-ken, 305-8566, Japan) under accession No. FERM BP-7437.

Further aspect of the present invention is an antibody which binds specifically to CLAC-P or CLAC of the present invention.

Specific antibody to CLAC-P or CLAC can be obtained, for example by following methods:

On the basis of amino acid sequences of CLAC and CLAC-P, peptides such as following peptides are synthesized:

NC-1: Glu Pro Arg Ser Glu Asp Pro Thr Pro Ala Glu Gln His Cys (amino acids 14 to 27 of SEQ ID NO: 2) (SEQ ID NO: 3)

NC2-1: Gly Cys Asn His Gly Phe Leu Ser Ala Asp Gln Gln Leu Ile Lys (amino acids 171 to 183 of SEQ ID NO: 2, Gly and Cys are added before amino acid 171) (SEQ ID NO: 4)

NC2-2: Cys Lys Gly Glu Gln Gly Asp Gln Gly Pro Arg Met Val Phe Xaa Lys (amino acids 155 to 169 of SEQ ID NO: 2, Cys is added before amino acid 155) (Xaa represents hydroxyproline) (SEQ ID NO: 5)

NC3: Asp Tyr Asn Gly Asn Leu His Glu Ala Leu Gln Arg Ile Thr Cys (amino acids 430 to 443 of SEQ ID NO: 2, Cys is added after amino acid 443) (SEQ ID NO: 6)

NC4: Leu Gly Pro Asp Gly Leu Pro Met Pro Gly Cys Trp Gln Lys (amino acids 641 to 654 of SEQ ID NO: 2) (SEQ ID NO: 7)

Then, these peptides bound to KLH (keyhole Limpet Hemocyanin) are used as antigen to immunize rabbits. Antisera are obtained by estimating the reactivity with antigen peptides of sera obtained using ELISA method. Antisera are bound to Affigel to which antigen peptide is bound, and only specific antigen may be affinity-purified.

The splice variant of the eleventh aspect of the present invention can be also used as above described.

Antibodies specifically binding to CLAC-P or CLAC of the present invention may be polyclonal or monoclonal, preferably monoclonal antibodies. Particularly preferred antibody is 9D2 monoclonal antibody above described.

Some of such antibodies specifically bind to CLAC or CLAC-P. Some of such antibodies inhibit actions or functions of CLAC or CLAC-P. Therefore, further aspect of the present invention is a method for detecting CLAC or CLAC-P using such antibodies. This detection method may be applied to diagnosis of Alzheimer's disease. These antibodies can be labeled with known labels in the art such as radioactive labels (for example $^{99}$Tc), fluorescent labels or enzymatic labels. These labeled antibodies may be injected into living animals and scanned the image. Alternatively bindings of these antibodies to CLAC or CLAC-P protein are detected and quantified in biopsy or autopsy samples.

Thus, further aspect of the present invention is a diagnosis kit for Alzheimer's disease comprising a specific antibody to CLAC or CLAC-P that is detectably labeled. The kit components may be directly injected into a living human being and scanned the image. The kit components may also be reacted with a biopsy or autopsy sample. Preferred antibody is monoclonal antibody 9D2. Labels include, but not limited to, radioactive labels (for example $^{99}$Tc), fluorescent labels or enzymatic labels, which can be selected according to method for use, purpose of use, application site, etc. Such labels are well known to a skilled person in the art. The diagnostic kit of the present invention may be composed of separated vessel containing each component, or composed of several vessels in which several components are contained. In general, an appropriate instruction is appended to the kit.

Still further aspect of the present invention is a method for screening a inhibitor of CLAC or CLAC-P activity which inhibits actions and/or functions of CLAC or CLAC-P. Because such an inhibitor subsequently have effects such as inhibition of Aβ accumulation, it can be used as a therapeutic agent of Alzheimer's disease.

Such an inhibitor can be screened using for example the following method (i), (ii) or (iii):

(i) For a substance which influences binding of CLAC to beta-amyloid or promotion of amyloid aggregation, a test substance is added to synthetic Aβ (1-42) peptide and an appropriate amount of CLAC, mixed together, and the mixture is incubated for 0 to 5 days at room temperature, then inhibition of formation of amyloid fibers that emit fluorescence with thioflavin T is estimated. Alternatively, a test substance is administered orally, intravenously, or intraventrically to a mouse generated by mating a transgenic mouse over-expressing human CLAC-P gene with a transgenic mouse over-expressing Alzheimer mutant βAPP gene, or to a transgenic mouse over-expressing Alzheimer mutant βAPP gene. Then decrease of beta-amyloid plaques in brain is immunohistochemically or biochemically estimated, by comparing with that in brain of a mouse that has not been given the test substance.

(ii) For a substance which inhibits binding to beta-amyloid of cells via CLAC-P, HEK293 cells stably expressing CLAC-P and control cells are cultured, and 10 μM of Aβ (1-42) and a test substance that have been preincubated in a test tube for 60 min are added. Then, the mixture is incubated further 60 min, and the amount of Aβ bound to the recovered cells can be estimated.

(iii) For a substance that inhibits cytotoxicity of Aβ bound to cells via CLAC-P, for example, PC12 cells having been differentiated to be neurons by NGF are made to transiently express CLAC-P by lipofection method. Then, Aβ (1-42) and a test substance preincubated for 1 hour are added, thereafter the cells are TUNEL stained to estimate inhibition of apoptosis, or increase of living cells is estimated by MTT reagent.

Therefore, further aspect of the present invention is a method for screening such an inhibitor, comprising using CLAC or CLAC-P.

Such inhibitors include, but not limited to antagonists to CLAC or CLAC-P, polypeptides having similar structures to CLAC or CLAC-P, or other low molecular compounds.

Some antibodies that bind specifically to CLAC or CLAC-P of the present invention, inhibit the actions and/or functions of CLAC or CLAC-P. Subsequently these antibodies can inhibit accumulation of Aβ in brain, and treat, retard or prevent Alzheimer's disease.

Thus, another aspect of the present invention is a method to treat, retard or prevent Alzheimer's disease comprising administering such an inhibitor or an antibody. Such an inhibitor or an antibody may be administered solely or with an appropriate carrier such as purified water or saline. The routes of administration include intravenous route and intracerebrospinal cavity route, preferably intravenous route. The dose is normally 1 ug to 100 mg/kg, however the dose can be altered depending on route of administration, severity of the disease to be treated, condition of the patient, etc.

Suitable antibody to the above-mentioned method is monoclonal antibody 9D2.

A substance which has therapeutic effect of Alzheimer's disease by inhibiting production of CLAC or CLAC-P itself, is also included in the present invention. An example of the method for screening such a substance is as follows:

For a substance which has a therapeutic effect via decrease of CLAC or CLAC-P production, screening can be performed by culturing the transformed cells of the present invention in a medium containing a test substance, and detecting or quantifying production or secretion of CLAC. In said screening method, change in production or secretion of CLAC from cells by the test substance can be detected and quantified, using suitable methods such as Western blotting method using an antibody specific to CLAC.

Specifically, for example the transformed cells are plated in a multi-well plate, and cultured in DMEM medium containing sera to be confluent. After the cells are washed in a serum-free medium (DMEM containing 0.5% bovine serum albumin), a test substance is added to the same medium, and cultured for a certain period (for example 24 hours). The amount of CLAC contained in the culture supernatant or in the extracellular matrix is quantified by Western blotting method. And, inhibitory effect of the test substance on CLAC production and/or secretion is estimated by the amount of CLAC compared with that in the group not containing the test substance, or by the concentration of the test substance to induce decrease of CLAC production and/or secretion. Such a screening method is also included in the present invention.

Further a peptide molecule which interacts with CLAC or CLAC-P and is physiologically useful, can be identified and/or obtained, for example a method comprising either step of (i), (ii) or (iii):

(i) A gene library in which a gene of human CLAC-P is fused to a gene of DNA binding protein and a gene library in which a gene of transcription activating protein is fused to cDNAs from human brain are expressed in yeast cells, and genes showing positive reactions are obtained by use of two hybrid method.

(ii) An extract of human brain is passed to a column to which human CLAC-P or CLAC recombinant protein is bound, and the bound protein is eluted and submitted to amino acid sequence analysis.

(iii) An extract of human brain is passed to a column to which human CLAC-P is immobilized, and the protein which binds to the column together with human CLAC-P or CLAC is eluted and submitted to amino acid sequence analysis.

Such a peptide molecule is also useful in treatment, retardation or prevention of Alzheimer's disease. Therefore, such a peptide molecule, and a method for identifying and/or obtaining it are also included in the present invention.

A protein that influences secretion and/or production of CLAC-P and/or CLAC is also useful in a method for treatment, retardation or prevention of the present invention. Such a protein can be identified, for example by making cultured cells expressing CLAC-P to express human cDNA library, selecting a clone expressing single cDNA by limiting dilution, and estimating change in the amount of secreted CLAC from the cell clone, then identifying the gene introduced. Therefore, such a protein, and a method for identifying it are also included in the present invention.

Further aspect of the present invention is a transgenic animal in which either CLAC DNA or CLAC-P DNA is artificially introduced into the chromosome, or either DNA is deleted from the chromosome. A transgenic animal is an animal in which a foreign gene is introduced by recombinant DNA method. Transgenic animal has a character that is not obtained by usual breeding. A method for producing a transgenic animal is well known to a skilled person in the art. Generally, transgenic animal can be produced by a process comprising following steps: cloning a gene containing a DNA to be introduced, ligating the gene to a promoter which expresses in desired organ and at desired time, introducing the construct into a fertilized egg, and transplanting the fertilized egg into a pseudopregnant female animal. By suitably selecting or mutating the expression regulating sequence, a transgenic animal can be obtained in which expression of CLAC or CLAC-P of the present invention is artificially regulated. Knockout animal is also included in transgenic animal. Such transgenic animals are useful in regulation of functions or expression of CLAC or CLAC-P of the present invention, investigation of development of diseases in which CLAC or CLAC-P involves, screening and development of medicines, etc. Preferably such transgenic animals are those other than a human being.

CLAC-P and CLAC from other animals than a human being can be cloned. For example, using cDNA library from desired animal, by amplifying a gene in a similar method to above mentioned, genes of CLAC-P and CLAC of desired animal can be cloned, and amino acid sequences thereof can be deduced (for cloning of mouse CLAC-P gene, see Example 7 of the specification).

EXAMPLES

The present invention is described by reference of the Examples below. The Examples should not be construed to limit the present invention.

Example 1

Preparation of Monoclonal Antibody 9D2

(1) Partial Purification of Senile Plaque Amyloid

Gray matter was cut out of Alzheimer's brain cortex, homogenized with a potter homogenizer (Matsushita Electric Industrial) in TSI solution containing 1 M sucrose (Kanto Chemicals) [50 mM Tris (Gibco BRL), 150 mM NaCl (Kanto Chemicals), 0.5 mM DIFP (Wako Pure Chemical Industries, Ltd.), 0.5 mM PMSF (Boehringer Mannheim), 1 mM EGTA (Wako Pure Chemical Industries, Ltd.), 1 µg/ml antipain (Sigma), 1 µg/ml leupeptin (Wako Pure Chemical Industries, Ltd.), 1 µg/ml pepstatin (Sigma), 1 µg/ml TLCK (Sigma)], and centrifuged at 260,000×g in a centrifuge (Hitachi Koki) at 4° C. for 30 min.

The Pellet obtained was suspended in TSI solution supplemented with 1M sucrose, and fractionated by discontinuous sucrose density gradient centrifugation (Am. J. Pathol., 148 1517 (1996)) to collect 1.5M sucrose/2.2M sucrose interface.

The interface collected was treated with DNase I (Wako Junyaku) at 37° C. for 3 hours, and suspended into TSI solution containing 1% Triton-X 100 and 5M urea (Nacalai Tesque), and capillaries were removed (J. Neurochem., 58 1953 (1992)), and centrifuged (100,000×g) in a centrifuge at 4° C. for 30 min.

Pellets obtained were used as an amyloid fraction.

(2) Preparation of Antibodies

The senile plaque amyloid fraction was suspended into a 50 mM Tris solution containing 1% SDS, emulsified with a Freund's complete adjuvant (Sigma), and inoculated to mouse's foodpad (BALB-C, 7 weeks, male) [J. Exp. Med., 169 1693 (1989)].

After 25 days from immunization, lymph nodes of posterior limbs were removed, and lymphocytes were taken out in RPMI medium. The lymphocytes were fused to myeloma cells (PAI strain) from mouse myeloma, and hybridomas were prepared. The hybridomas were suspended in HAT medium, and dispersed into 96-well plates (Greiner) and cultured for 10 days.

(3) Screening of Monoclonal Antibodies

Hybridoma supernatants were collected from wells, and antibodies that stain amyloid positively were selected on smears of senile plaque amyloid fraction (Am. J. Pathol., 148 1517 (1996)).

From 288 hybridoma clones, most positive monoclonal antibody 9D2 was selected. Isotype of the monoclonal antibody was identified as IgG1 by use of Mouse antibody isotype kit (Amersham). A hybridoma that produce the highest amount of 9D2 antibody was designated as hybridoma 9D2, and deposited to International Patent Organism Depository, National Institute of Advanced Industrial Science and Technology (AIST Tsukuba Central 6, 1-1, Higashi 1-Chome, Tsukuba-shi, Ibaraki-ken, 305-8566, Japan) and assigned an accession No. FERM BP-7437 on Jan. 30, 2001.

Surprisingly it was found that such antibodies bound strongly and specifically to unknown proteins (referred as CLAC-P and CLAC in this specification) from Alzheimer's brain. In particular, monoclonal antibody 9D2 binds very strongly and specifically to CLAC-P and CLAC. Moreover monoclonal antibody 9D2 is characterized in that it strongly reacts with a peptide fragment Xaa Ala Pro Ser Glu Cys (SEQ ID NO: 29) in which amino acid 113 Glu of CLAC-P is changed to pyroglutamic acid.

Cloning, sequencing, etc of these genes encoding these unknown proteins (i.e. CLAC-P and CLAC) are described in Example 2.

Example 2

Cloning of Human CLAC-P Gene

Twenty grams of Gray matter was cut out of Alzheimer's cerebral cortex, homogenized with a potter homogenizer in TSI solution, and centrifuged at 260,000×g in a centrifuge at 4° C. for 20 min. Pellets obtained was suspended in TSI solution supplemented with 1M sucrose, and centrifuged at 260,000×g in a centrifuge at 4° C. for 20 min. Pellets obtained were suspended into TSI solution containing 0.32M sucrose, and capillaries were removed, and centrifuged at 260,000×g in a centrifuge at 4° C. for 20 min. Pellets obtained were homogenized in TSI solution containing 2% SDS (Nacalai Tesque) using a homogenizer, and centrifuged at 260,000×g in a centrifuge at 4° C. for 20 min. Pellets obtained were broken in 70% formic acid (Wako Pure Chemical Industries, Ltd.) by a sonicator (Branson), and centrifuged at 260,000×g in a centrifuge at 4° C. for 20 min. The supernatant was freeze-dried in a freeze-drier (Tomy), thereafter suspended in an aqueous solution of 6M guanidine hydrochloride (Nacalai Tesque), and centrifuged at 260,000×g in a centrifuge at 4° C. for 20 min. 70% formic acid (1/100 volume of the supernatant) was added, and separated by RP-HPLC (Hewlett-Packard) using Aquapore RP300 column (2.1×30 mm, Applied Biosystems) [J. Biol. Chem., 267 17047 (1992)].

A fraction positive for monoclonal antibody 9D2 was selected by immunoblotting method using SDS-PAGE (Proc. Natl. Acad. Sci. USA, 94 2025 (1997)), and it was found that the fraction was eluted with ca. 30% acetonitrile (Wako Pure Chemical Industries, Ltd.). After the fraction positive for 9D2 was freeze-dried, the fraction was suspended in 6 M guanidine hydrochloride aqueous solution, reduced by reductive carboxy-methylation method (J. Biol. Chem., 238 622 (1963)), and separated by gel-filtration HPLC using TSKgel SuperSW3000 column (4.6×600 mm, Tosoh). A fraction of ca. 35 kDa to which 9D2 antibody strongly reacted in immunoblotting method was digested with a lysyl endopeptidase API (*achromobacter lyticus* protease I), or Asp-N (Boehringer Mannheim) [J. Biol. Chem., 267 17047 (1992)]. Digests were separated by RP-HPLC using Superspher Select B column (2.1×125 mm, Merck) to obtain a peptide map.

A fraction obtained by peptide map was analyzed by a TOF (time of flight) type mass spectrometer (Bruker-Franzen Analytik) and an amino acid sequencer (Applied Biosystems) [J. Biol. Chem., 274 7368 (1999)], and partial amino acid sequences were selected that had identical molecular weights to those obtained by the mass spectrometer.

Sequences obtained are as follows (upper: amino terminal; bottom: carboxy terminal):

By digestion enzyme API

```
                                          (SEQ ID NO: 8)
Ile Asn His Gly Phe Leu Ser Ala Asp Gln Gln Leu
Ile Lys,
```
and

```
                                          (SEQ ID NO: 9)
Gly Glu Gln Gly Asp Gln Gly Hyp Arg Met Val Phe
Pro Lys
``` were obtained (Hyp represents hydroxyproline).

By digestion enzyme Asp-N

```
                                         (SEQ ID NO: 10)
Asp Gln Gly Pro Arg Met Val Phe Pro Lys Ile Asn

His Gly Phe Leu Ser Ala
``` was obtained.

As a result, following amino acid sequence of 28 amino acids was obtained as a partial amino acid sequence of 9D2 antigen:

```
                                         (SEQ ID NO: 11)
Gly Glu Gln Gly Asp Gln Gly Pro Arg Met Val Phe

Pro Lys Ile Asn His Gly Phe Leu Ser Ala Asp Gln

Gln Leu Ile Lys
```

On the basis of this sequence, cDNA of 9D2 antigen portion was cloned by PCR (polymerase chain reaction) method using degenerated primers. The primers used were designed as follows:

```
                                         (SEQ ID NO: 12)
    5'-aar ggi gar car ggi gay car ggi cc-3'

(SEQ ID NO: 13)
    5'-agc tgc tgr tci gcd gav agr aab cc-3'

(SEQ ID NO: 14)
    5'-agc tgc tgr tci gcr ctv agr aab cc-3'
``` wherein i represents inosine, r represents a or g; y represents c or t; d represents a, g or t; and v represents a, g or c.

Using Human brain Marathon-Ready cDNA Library (CLONTECH) as a template, a 80 bp cDNA fragment was amplified by LA Taq (TaKaRa) in a PCR apparatus (TaKaRa)—40 cycles of: heat denaturation at 95° C. for 30 sec, annealing at 58° C. for 30 sec, and DNA synthesis at 72° C. for 1 min. This fragment was sub-cloned into pBluescript II KS+ (Stratagene), and sequenced by an automatic sequencer (Li-COR) using Thermo sequencing kit (Amersham).

By repeating RACE method using PCR based on the sequence of the fragment, cloning of CLAC-P DNA was performed that included ORF (open reading frame) of CLAC-P. Specific primers used are as follows:

```
                                         (SEQ ID NO: 15)
    5'-tag ctg ctg gtc ggc gct gag gaa gcc a-3'

(SEQ ID NO: 16)
    5'-aag ggg gaa cag ggg gac cag ggg ccg a-3'
```

-continued

```
                                      (SEQ ID NO: 17)
5'-tcg gaa aca cca tcc tcg gcc cct ggt c-3'

(SEQ ID NO: 18)
5'-cat ggc ttc ctc agc gcc gac cag cag c-3'

(SEQ ID NO: 19)
5'-cgc cgc ctg att aag ggt gac caa gga c-3

(SEQ ID NO: 20)
5'-aag agg gcc acc tgg gga cac agg gaa a-3'

(SEQ ID NO: 21)
5'-acc ctt ggg gcc gtt ctc tcc agc gtc t-3'

(SEQ ID NO: 22)
5'-cac ctt gtt ctc cag gtt ctc cct tag g-3'

(SEQ ID NO: 23)
5'-gaa tac cag gac cta agg gag aac ctg g-3'

(SEQ ID NO: 24)
5'-ggc ccc aag ggt gac aca ggc gaa aag g-3'

(SEQ ID NO: 25)
5'-ccc tcc ttt ccc tgc gtg ctt ctt cag c-3'

(SEQ ID NO: 26)
5'-tct cgg ctt cgc ttc cca ccc tct aca c-3'

(SEQ ID NO: 27)
5'-gga gat tct gga atg ccg ggt cca cag g-3'

(SEQ ID NO: 28)
5' ctt cta tca tag gcc cac cag gcc cac c-3'
```

The fragment was amplified by LA Taq (TaKaRa) in PCR apparatus (TaKaRa) using Human brain Marathon-Ready cDNA Library (CLONTECH) as a template—35 cycles of: heat denaturation at 95° C. for 30 sec, annealing at 58° C. for 1 min, and DNA synthesis at 72° C. for 5 min, thereafter nested primer added—30 cycles of: heat denaturation at 95° C. for 30 sec, annealing at 60° C. for 1 min, and DNA synthesis at 72° C. for 5 min. The fragment obtained was subcloned into pBluescript II KS+, and sequenced by an automatic sequencer using Thermo sequencing kit.

Thus, cDNA of novel protein CLAC-P was obtained (SEQ ID NO: 1). The amino acid sequence of the ORF (SEQ ID NO: 2) was deduced from the nucleotide sequence. These DNA and amino acid sequences are shown in FIG. 1.

cDNA of CLAC-P contains an ORF encoding 654 amino acids in length (FIG. 1, SEQ ID NO: 1, and SEQ ID NO: 2). CLAC-P is a novel protein that is type II single pass transmembrane protein. Its amino terminal is located on the cytoplasmic side, and its carboxy terminal is on the extracellular side. The amino acid sequence has three repeats of collagen-like Gly-$Xaa_1$-$Xaa_2$ (G represents glycine; $Xaa_1$ and $Xaa_2$ represent any amino acids) in the extracellular region. mRNA expression was investigated in various human tissues using RT-PCR method, and specific expression was found in brain and testis. A peptide antibody prepared on the basis of the deduced amino acid sequence stained senile plaques in Alzheimer's brain, and it was found that the protein fragment derived from the cDNA obtained accumulated in senile plaque amyloid.

Example 3

Assay of Amyloid Beta Peptide Receptor Function of CLAC-P Using Human Transformed Cells that Permanently Express Human CLAC-P A plasmid DNA in which CLAC-P gene was integrated was prepared as described below: CLAC-P gene was altered to be cleaved at position −40 of 5' UTR region of CLAC-P by HindIII, and at position +100 from the first stop codon of the 3' UTR region. The altered CLAC-P gene was integrated into HindIII-BamHI region of multicloning site of pcDNA3.1/Hygro(+) (invitrogen) having CMV promoter.

HEK293 cells were plated into 6-well plates (Nunc) at a concentration of $3.0\text{-}5.0\times10^5$ cells/well, and cultured for 24 hours. Then, solution A: 1 ug plasmid DNA/100 μl Opti-MEM (Gibco BRL) and solution B: 10 μl LipofectAMINE (Gibco BRL)/100 μl Opti-MEM are prepared, mixed together and incubated for 30 min, then 800 μl of Opti-MEM was added to the mixture to 1 ml (DNA-Lipofectamine complex) (per well). DMEM was removed from the cells, and the cells was washed with Opti-MEM (1×), then 1 ml of DNA-Lipofectamine complex was added to each well and cultured for 6 hours. Then 1 ml of DMEM containing 20% FBS was added, and cultured for further 24 hours. After replacement of the medium to DMEM, cultured for further 24 hours. Thereafter the cells in each well were re-plated into 10 cm dish, and selection culture was performed in DMEM containing 133 μg/ml of hygromycin (Wako Junyaku). After selection culture for 10-14 days, grown cells are taken as polyclonal cell strains in which desired plasmid was introduced. Polyclonal cell strains were further cloned by limited dilution method, and 15 monoclonal cell strains were obtained. The monoclonal cell strains were analyzed for their expression by immunoblotting using an antibody specific to CLAC-P protein. Three strains that showed maximum expression were selected, designated as 9D2-1, 9D2-2, and 9D2-11, and used subsequent experiments. Strain 9D2-1 which was a transformant of HEK293 cell permanently expressing human CLAC-P was deposit to International Patent Organism Depository, National Institute of Advanced Industrial Science and Technology (AIST Tsukuba Central 6, 1-1, Higashi 1-Chome, Tsukuba-shi, Ibaraki-ken, 305-8566, Japan) and assigned an accession No. FERM BP-7438 on Jan. 30, 2001.

Cover glasses pre-coated with poly-L-lysine (Sigma, 10 ug/ml) were arranged on 10 cm dishes, upon which cells were applied, cultured, gene-introduced, and recovered the cover glasses. The cover glasses were washed with PBS solution (2×), then fixed with PBS solution containing 4% paraformaldehyde (TAAB) at room temperature for 30 min. After further washing with PBS solution (2×), permeabilization and blocking were performed with PBS solution containing 0.5% Triton X-100, 0.3% BSA (Bovine serum albumin, Sigma) at room temperature for 30 min. The solution was removed, and an antibody was added which was diluted (1/1000) with PBS solution containing 0.3% BSA, and reacted at room temperature for 2 hours. After washing with PBS (3×), FITC-bound-anti-rabbit antibody (Jackson) as a secondary antibody was added which was diluted with PBS solution containing 0.3% BSA, then reacted at room temperature for 1 hour with glare protection. After washing with PBS (3×), the sample was encapsulated with a encapsulating agent and observed using a fluorescent microscope. (AX-80, Olympus). Distribution of CLAC-P was observed in cell membrane system, particularly endoplasmic reticulum, Golgi apparatus and cell surface membrane.

After monoclonal HEK293 strain stably expressing CLAC-P cultured in 10 cm dish was washed in TS solution, the strain was recovered by cell-scraper in TSI solution. The cells were disrupted in a polytron homogenizer (Hitachi Koki), then centrifuged at 1,000×g, 4° C., for 7 min. The supernatant was collected, and centrifuged at 2,000×g, 4° C., for 30 min. The pellet was used as a mitochondria and lysosome fraction. The supernatant was further ultra-centrifuged at 100,000×g, 4° C., for 60 min. The pellet was recovered as a microsome fraction and analyzed, and the supernatant was recovered as cytoplasmic fraction and analyzed. As shown in right panel (B) of FIG. 2, expression of a full length CLAC-P protein of 80 kDa was detected specifically in membrane fraction of CLAC-P expressing cells.

HEK293 cells permanently expressing human CLAC-P, and control cells permanently expressing pcDNA3.1 vector only were cultured in 10 cm dishes, and when reached to confluent, 10 μM Aβ (1-42) (Bachem) preincubated at 37° C. for 60 min was added, and incubated for a certain period. After incubation, culture supernatant containing Aβ was removed, and the cells were washed in PBS (3×), then collected by a scraper, and precipitated in a microcentrifuge (TOMY) at 7,000 rpm for 5 min. Sample buffer was added to the cell pellet, and solubilized by sonication, and the protein was quantified using BCA protein assay kit (Piearce).

The amounts of the proteins contained each sample were adjusted to be a certain level, and 2-mercaptoethanol was added (final concentration was 1%), and heated for 10 min. The proteins were separated by SDS-PAGE using 15% Tris-Tricine gel, and transferred to a nitrocellulose membrane (Hybon-ECL, Amersham) under a condition of 3 hours at 150 mA. Transferred membrane was heated in PBS for 10 min, then blocked in 1% skim milk (Difco)-PBS at room temperature for 30 min, and reacted with various antibodies diluted by similar blocking solution at room temperature for 2 hours, or at 4° C. overnight. The membrane was reacted solution at room temperature for 1 hour with a secondary antibody (anti-mouse or anti-rabbit Ig, horseradish peroxidase bound whole antibody (Amersham)) that were washed in PBS-T (PBS containing 0.1% Tween 20) for 10 min (3×), then diluted with similar blocking. After washing in PBS-T for 10 min (3×), exposed to Hyperfilm-ECL (Amersham) using ECL kit (Amersham), and Aβ binding was detected. Cells expressing human CLAC-P bound 30 ng of Aβ (1-42) per mg protein, while cells expressing the vector only bound 6 ng of Aβ. As the result of above experiment, binding of Aβ increased five times, which indicated that human CLAC-P expressed on cell surface acts as a receptor for Aβ.

Example 4

Amino Acid Sequence of CLAC from Amyloid in Human Alzheimer's Brain, and the Reactivity with 9D2 Antibody CLAC purified from human Alzheimer's brain according to the method of (1) described in Example 2, was subjected to amino acid analysis, however it was impossible to analyze the protein because the amino terminal was blocked. A peptide corresponding to amino acids 113-118 of CLAC-P, Xaa Ala Pro Ser Glu Cys (SEQ ID NO: 29) was synthesized in which amino acid 113 Glu was substituted with pyroglutamic acid (Xaa). The peptide was bound to KLH through Cys residue, then the bound peptide was used as an immunogen to produce an antibody (hereinafter, said antibody is referred as PyroG). As inferred from the description of Neuron, 14 457 (1995), antigen PyroG specifically recognized the structure of the amino terminal opposite to the KLH binding side of the synthesized peptide. Namely, PyroG did not react with full length recombinant CLAC-P protein obtained by expression in cultured cells according to the method of Example 3 when immunoblotting method was performed using SDS-PAGE. However, Xaa Ala Pro Ser Glu Cys (SEQ ID NO: 29) peptide was immobilized to a micro-well plate (according to the method of EMBO J., 11, 2895 (1992)), and enzyme-linked immunosorbent assay (ELISA) was performed by indirect peroxidase method using PyroG antibody as a primary antibody. In the ELISA, positive reaction was found. Also, CLAC obtained from human Alzheimer's brain as above described reacted positively with PyroG in immunoblotting method. Further, positive reaction of 9D2 antibody and CLAC from Alzheimer's brain in immunoblotting method, and immunohistochemical staining with Alzheimer's brain tissue specimen were diminished by preliminary mixing Xaa Ala Pro Ser Glu Cys (SEQ ID NO: 29) with 9D2 antibody to absorb the antibody activity (according to Neuron, 13, 45 (1994)). These facts indicated that CLAC from Alzheimer's brain amyloid starts from amino acid 113 of CLAC-P and the amino acid 113 is pyroglutamic acid and that 9D2 antibody recognizes CLAC protein underwent such a modification.

Example 5

In Vitro Binding of CLAC to Beta-Amyloid (Aβ)

In vitro binding of CLAC to Aβ was performed according to a method of Webster et al. (Am. J. Pathol., 150, 1531 (1997)).

The transformant (strain 9D2-1) permanently expressing human CLAC-P obtained in Example 3 was selection-cultured in DMEM medium containing 10% FBS and hygromycin for 4 days, and the culture supernatant was collected. Fifty μl (0.1 mg/ml) of synthetic Aβ (1-42) (Bachem) was immobilized to each well of 96-well micro-well plates (Greiner), and dried in a desiccator. Thereafter, blocking was performed with PBS-T containing 1% gelatin (Wako Junyaku) for 1 hour, and washed with PBS-T for 10 min (3×), and the culture supernatant obtained was applied. Similarly, culture supernatant of control HEK293 cells used in Example 3 was applied. After reaction at room temperature for 1 hour, washed with PBS-T for 10 min (5×), and then reacted with anti-CLAC antibody diluted with similar blocking solution (1/5000) at room temperature for 1 hour. After washing with PBS-T for 10 min (5×), reacted with a secondary antibody (anti-rabbit Ig, horseradish peroxidase bound whole antibody (Amersham)) diluted with similar blocking solution (1/5000) at room temperature for 1 hour. After washing with PBS-T for 10 min (5×), color was developed with TMB reagent (Kirkegard & Perry Laboratories).

As a result of ten trials, the culture supernatant of transformant permanently expressing CLAC-P that secretes CLAC developed stronger color about fifty times than control HEK293 that does not secrete CLAC, which indicates that CLAC significantly binds to Aβ ($p<0.0001$) in vitro.

Example 6

Effects of CLAC on Aβ Aggregation

The transformant (strain 9D2-1) permanently expressing human CLAC-P obtained in Example 3 was selection-cultured in DMEM medium containing hygromycin and 10% FBS for 3 days, and cultured starting from semi-confluency for 4 days in DMEM not containing FBS, and then the culture supernatant was collected. After centrifugation at 2,000×g, the supernatant was applied to a DEAE column (Whatman), and the through-pass fraction was further applied to a heparin column (Amersham). After washing the column fully with PBS solution containing 2M urea (Nacalai Tesque) (PB-U solution), elution was performed with PB-U solution containing 1M NaCl, and the eluate was dialyzed against PBS solution. The solution thus obtained was used as crude purified CLAC, and the solution obtained from control HEK293 cells was used as a control.

Experiment of Aβ aggregation was performed according to the standard method of LeVine (Methods in Enzymology, 309, 274).

One hundred μl of the crude purified CLAC or the solution from control HEK293 cells was added to 3.6 μM synthesized Aβ (1-42) (Bachem), and after passing through 0.22 μM filter, reacted at 37° C. for 1 day. Four hundred μl of glycine-NaOH solution (10 μM, pH=8.5) containing 3 μM thioflavin T was added to the reaction mixture, and the fluorescence was measured in a fluorophotometer (Hitachi F-2000) (excitation at 442 nm; measurement at 496 nm).

By eighteen trials, it was shown that Aβ aggregated with the crude purified CLAC sixty times as much as with the solution from the control HEK293 cells, and this result was significant ($p<0.0001$).

Example 7

Cloning of Mouse CLAC-P cDNA

Mouse brain Marathon-Ready cDNA Library (CLONTECH) was used as a template, mouse CLAC-P cDNA was cloned by PCR method. Following primers were prepared based on human CLAC-P cDNA sequence:

```
                                        (SEQ ID NO: 30)
5'-GGG ATC AAG GAG CCA CTA AGA TCA TAG A-3'
primer 1

(SEQ ID NO: 31)
5'-GGG CCT ATG ATA GAA GGA CCC TGT GGA C-3'
primer 2

(SEQ ID NO: 32)
5'-CTA CAA CGG CAA CCT CCA CGA AGC CTT-3'
primer 3

(SEQ ID NO: 33)
5'-TCT CCC TTT ATC CCC GGA AGT C-3'
Primer 4
```

Using primers 1 and 2, a cDNA fragment of about 330 bp was amplified by PCR apparatus (TaKaRa) using PremixLATaq (TaKaRa)—40 cycles of: heat denaturation at 95° C. for 45 sec, annealing at 42° C. for 45 sec, DNA synthesis at 72° C. for 3 min. Then, the reaction mixture as a template was added to PremixLATaq (1:50), and using primers 2 and 3, nested PCR was performed—35 cycles of: heat denaturation at 95° C. for 45 sec, annealing at 51° C. for 45 sec, DNA synthesis at 72° C. for 3 min. Thus, a fragment of about 300 bp was obtained. This fragment was purified, and sub-cloned into pBluescript II KS+ (Stratagene) by TA cloning method, and sequenced using an automatic sequencer (Li-COR) (SEQ ID NO: 50).

By searching on the basis of human CLAC-P, a sequence of about 70 bp from adult mouse testis was found in GenBank (AV264752, SEQ ID NO: 51) that has a high homology to human CLAC-P. Based on this sequence and the sequences previously obtained, new primers were synthesized:

```
                                        (SEQ ID NO: 34)
5'-CGA ATA TAT GGC TAA AAT AAG AAC GGT C-3'
primer 5

(SEQ ID NO: 35)
5'-CTG GCA AAC CGG TGT CTC CTT TCT CTC-3'
primer 6

(SEQ ID NO: 36)
5'-ACG GTC AGG GAG GCA CCT TTA GAG TGC A-3'
primer 7

(SEQ ID NO: 37)
5'-CTC TCC TTT TAC TCC ATT GGC ACC CGG C-3'
primer 8

(SEQ ID NO: 38)
5'-ACG GTC AGG GAG GAA GCT TTA GAG TGC A-3'
primer 9

(SEQ ID NO: 39)
5'-TCA ACT CCG GGG ATC CCT GGA GAG CCT T-3'
primer 10
```

Firstly, using primers 5 and 6, PCR reaction was performed—38 cycles of: heat denaturation at 95° C. for 45 sec, annealing at 55° C. for 45 sec, DNA synthesis at 72° C. for 3 min. Using this reaction mixture as a template, and using primers 7 and 8, PCR was performed in same conditions to amplify a fragment of about 1200 bp. The fragment was purified, and using primer 4 synthesized as a dye-primer, the nucleotide sequence was analysed by an automatic sequencer. Based on this nucleotide sequence, the following primers were prepared:

```
                                        (SEQ ID NO: 40)
5'-GGG ACC ATT TTC TCG AGC ATC TCC CTT T-3'
primer 11

(SEQ ID NO: 41)
5'-AAA ATG GTC CCA AAG GTG ATA CAG GAG-3'
primer 12
```

Using the reaction mixture obtained by PCR using primers 5 and 6 as a template, and using primers 9 and 11, PCR reaction was performed—38 cycles of: heat denaturation at 95° C. for 45 sec, annealing at 56° C. for 45 sec, DNA synthesis at 72° C. for 3 min. A fragment of about 560 bp thus obtained was digested with XhoI and HindIII. A XhoI-HindIII fragment was sub-cloned into pBluescript II KS+, and the nucleotide sequence was identified (SEQ ID NO: 52). Also, using the reaction mixture obtained by PCR using primers 5 and 6 as a template, and using primers 10 and 12, PCR reaction was performed—38 cycles of: heat denaturation at 95° C. for 45 sec, annealing at 56° C. for 45 sec, DNA synthesis at 72° C. for 3 min. A fragment of about 550 bp thus obtained was digested with XhoI and HindIII. A XhoI-HindIII fragment was sub-cloned into pBluescript II KS+ TA cloning method, and the nucleotide sequence was identified (SEQ ID NO: 53).

Next, RACE (rapid amplification of cDNA ends) method was performed on the basis of these sequences. Following primers were used:

```
                                        (SEQ ID NO: 42)
5'-TGC ACT CTA AAG GTG CCT CCC TGA CCG T-3'
primer 13

(SEQ ID NO: 43)
5'-GAC CGT TCT TAT TTT AGC CAT ATA TTC G-3'
primer 14
```

-continued

```
                                          (SEQ ID NO: 44)
5'-TGG TAA CCT CCA TGA GGC CTT ACA GAG A-3'
primer 15

(SEQ ID NO: 45)
5'-GAG AGA AAG GAG ACA CCG GTT TGC CAG-3'
primer 16

(SEQ ID NO: 45)
5'-GGC TGG ATG CTC CTT GCC AAT TGG GA-3'
primer 17

(SEQ ID NO: 46)
5'-TGG GAC CTG ATG GGT TAC CTA TGC CTG-3'
primer 18
```

Using mouse brain Marathon-Ready cDNA Library (CLONTECH) as a template, PCR reaction was carried out—cycles of heat denaturation at 95° C. for 45 sec, annealing at 59° C. for 45 sec, DNA synthesis at 72° C. for 5 min were repeated. Nested PCR was applied to the reaction mixture—cycles of heat denaturation at 95° C. for 45 sec, annealing at 60° C. for 45 sec, DNA synthesis at 72° C. for 5 min were repeated to amplify a fragment. The fragment was sub-cloned into pBluescript II KS+ by TA cloning method, and the nucleotide sequence was identified (SEQ ID NOs: 54, 55 and 56).

From these DNA fragments, the sequence of mouse CLAC-P cDNA was determined (FIG. 3 and SEQ ID NO: 48). From this cDNA sequence, the amino acid sequence of the ORF was deduced (FIG. 4 and SEQ ID NO: 49). Mouse CLAC-P cDNA encoded 666 amino acids (full length). Its homology to human CLAC-P cDNA was about 83%, and about 90% at amino acid level. The molecular structure of mouse CLAC-P was basically the same as human CLAC-P, and it was type II single pass transmembrane protein, and had three collagen-like repeat in the extracellular region. Moreover within the collagen-like sequence, a sequence that undergoes alternative splicing (FIG. 4, underlined; SEQ ID NO: 49) was identified.

Probability of Industrial Use of the Invention:

Novel collagen-like protein CLAC obtained in the present invention accumulates in Alzheimer's senile plaque amyloid, and promotes aggregation of beta-amyloid that is the main component of Alzheimer's senile plaque amyloid. CLAC-P, a precursor of CLAC, is distributed on the surface of cell membrane as a transmembrane protein, and acts as a receptor that binds beta-amyloid to the cell surface. Thus CLAC-P is involved in the progress of Alzheimer's disease. CLAC-P can be useful in prevention, retardation and treatment of Alzheimer's disease.

Sequence Listing Free Text:
SEQ ID NO: 5
Xaa is hydroxyproline.
SEQ ID NO: 9
Xaa is hydroxyproline.
SEQ ID NO: 12
Designed oligonucleotide primer to amplify human CLAC-P cDNA fragment.
r is g or a. i is inosine. y is t or c.
SEQ ID NO: 13
Designed oligonucleotide primer to amplify human CLAC-P cDNA fragment.
r is g or a. i is inosine. v is a, g or c. d is a, g or t.
SEQ ID NO: 14
Designed oligonucleotide primer to amplify human CLAC-P cDNA fragment.
r is g or a. i is inosine. v is a, g or c.
SEQ ID NO: 15
Designed oligonucleotide primer to amplify human CLAC-P cDNA fragment.
SEQ ID NO: 16
Designed oligonucleotide primer to amplify human CLAC-P cDNA fragment.
SEQ ID NO: 17
Designed oligonucleotide primer to amplify human CLAC-P cDNA fragment.
SEQ ID NO: 18
Designed oligonucleotide primer to amplify human CLAC-P cDNA fragment.
SEQ ID NO: 19
Designed oligonucleotide primer to amplify human CLAC-P cDNA fragment.
SEQ ID NO: 20
Designed oligonucleotide primer to amplify human CLAC-P cDNA fragment.
SEQ ID NO: 21
Designed oligonucleotide primer to amplify human CLAC-P cDNA fragment.
SEQ ID NO: 22
Designed oligonucleotide primer to amplify human CLAC-P cDNA fragment.
SEQ ID NO: 23
Designed oligonucleotide primer to amplify human CLAC-P cDNA fragment.
SEQ ID NO: 24
Designed oligonucleotide primer to amplify human CLAC-P cDNA fragment.
SEQ ID NO: 25
Designed oligonucleotide primer to amplify human CLAC-P cDNA fragment.
SEQ ID NO: 26
Designed oligonucleotide primer to amplify human CLAC-P cDNA fragment.
SEQ ID NO: 27
Designed oligonucleotide primer to amplify human CLAC-P cDNA fragment.
SEQ ID NO: 28
Designed oligonucleotide primer to amplify human CLAC-P cDNA fragment.
SEQ ID NO: 29
Xaa is pyroglutamic acid.
SEQ ID NO: 30
Designed oligonucleotide primer to amplify mouse CLAC-P DNA fragment.
SEQ ID NO: 31
Designed oligonucleotide primer to amplify mouse CLAC-P DNA fragment.
SEQ ID NO: 32
Designed oligonucleotide primer to amplify mouse CLAC-P DNA fragment.
SEQ ID NO: 33
Designed oligonucleotide primer to amplify mouse CLAC-P DNA fragment.
SEQ ID NO: 34
Designed oligonucleotide primer to amplify mouse CLAC-P DNA fragment.
SEQ ID NO: 35
Designed oligonucleotide primer to amplify mouse CLAC-P DNA fragment.
SEQ ID NO: 36
Designed oligonucleotide primer to amplify mouse CLAC-P DNA fragment.

SEQ ID NO: 37
Designed oligonucleotide primer to amplify mouse CLAC-P DNA fragment.
SEQ ID NO: 38
Designed oligonucleotide primer to amplify mouse CLAC-P DNA fragment.
SEQ ID NO: 39
Designed oligonucleotide primer to amplify mouse CLAC-P DNA fragment.
SEQ ID NO: 40
Designed oligonucleotide primer to amplify mouse CLAC-P DNA fragment.
SEQ ID NO: 41
Designed oligonucleotide primer to amplify mouse CLAC-P DNA fragment.
SEQ ID NO: 42
Designed oligonucleotide primer to amplify mouse CLAC-P DNA fragment.
SEQ ID NO: 43
Designed oligonucleotide primer to amplify mouse CLAC-P DNA fragment.
SEQ ID NO: 44
Designed oligonucleotide primer to amplify mouse CLAC-P DNA fragment.
SEQ ID NO: 45
Designed oligonucleotide primer to amplify mouse CLAC-P DNA fragment.
SEQ ID NO: 46
Designed oligonucleotide primer to amplify mouse CLAC-P DNA fragment.
SEQ ID NO: 47
Designed oligonucleotide primer to amplify mouse CLAC-P DNA fragment.

What is claimed is:

1. A purified collagenous Alzheimer amyloid plaque component (CLAC) protein comprising the amino acid sequence of amino acid 113 to amino acid 654 shown in SEQ ID NO: 2.

2. The protein of claim 1, having following properties:
   (a) accumulating in senile plaque amyloid component of Alzheimer's disease, and
   (b) having a function of promoting aggregation of Aβ.

3. A purified collagenous Alzheimer amyloid plaque component precursor (CLAC-P) protein comprising the amino acid sequence shown in SEQ ID NO: 2.

4. The protein of claim 3, functioning as an Aβ cell surface receptor.

5. An isolated protein that differs from the protein defined in claim 4 in that one or more amino acids are deleted from or substituted in a region of amino acids 141 to 146 or amino acids 589 to 597 of SEQ ID NO: 2.

* * * * *